US010585253B2

(12) United States Patent
Bingham et al.

(10) Patent No.: US 10,585,253 B2
(45) Date of Patent: Mar. 10, 2020

(54) CTIR SPECTROMETER FOR LARGE AREA ASSESSMENT OF GAS EMISSIONS

(71) Applicant: UT-Battelle, LLC, Oak Ridge, TN (US)

(72) Inventors: Philip R. Bingham, Knoxville, TN (US); Panagiotis G. Datskos, Knoxville, TN (US); Tommy J. Phelps, Knoxville, TN (US); Kenneth W. Tobin, Jr., Harriman, TN (US)

(73) Assignee: UT-BATTELLE, LLC, Oak Ridge, TN (US)

(*) Notice: Subject to any disclaimer, the term of this patent is extended or adjusted under 35 U.S.C. 154(b) by 153 days.

(21) Appl. No.: 15/586,085

(22) Filed: May 3, 2017

(65) Prior Publication Data

US 2017/0322383 A1    Nov. 9, 2017

Related U.S. Application Data

(60) Provisional application No. 62/330,882, filed on May 3, 2016.

(51) Int. Cl.
*G02B 6/42*    (2006.01)
*F21V 8/00*    (2006.01)
(Continued)

(52) U.S. Cl.
CPC .......... *G02B 6/4298* (2013.01); *G01J 3/0291* (2013.01); *G01J 3/0294* (2013.01);
(Continued)

(58) Field of Classification Search
CPC ......................... G01N 21/3504; G02B 6/4298
(Continued)

(56) References Cited

U.S. PATENT DOCUMENTS 7,085,344 B2 *  8/2006  Prasser ................ G01N 23/046
                                                       250/370.09
8,330,957 B2 * 12/2012  Hager .................... G01N 21/33
                                                           356/438
(Continued)

OTHER PUBLICATIONS

Faist, J. et al., "Quantum Cascade Lasers", Science, Apr. 1994, pp. 553-556, vol. 264.
(Continued)

*Primary Examiner* — David P Porta
*Assistant Examiner* — Abra S Fein
(74) *Attorney, Agent, or Firm* — Scully, Scott, Murphy & Presser, P.C.

(57) ABSTRACT

Systems for determining the presence and distribution of gas emissions in an area are provided. For example, a system may include one or more light detectors and one or more reflectors and/or one more retroreflectors disposed around the perimeter, a light source configured to emit light at a plurality of wavelengths towards the one or more light detectors and/or the one or more reflectors and/or one or more retroreflectors, and one or more processors configured to receive information representing light intensity detected by the one or more light detectors, respectively at each of the plurality of wavelengths and determine gases present in each path based on the light intensity detected by the respective detector at each of the plurality of wavelengths and distribution thereof. The path being either light source-respective detector, light source-respective reflector-respective detector or light source-respective retroreflector-respective detector. Other system may not use reflectors and/or retroreflectors.

20 Claims, 21 Drawing Sheets

(51) Int. Cl.
```
     G02B 6/35       (2006.01)
     G01N 21/3504    (2014.01)
     G06T 11/00      (2006.01)
     G01J 3/02       (2006.01)
     G01J 3/10       (2006.01)
     G01J 3/42       (2006.01)
     G02B 5/08       (2006.01)
```
(52) U.S. Cl.
CPC . *G01J 3/10* (2013.01); *G01J 3/42* (2013.01); *G01N 21/3504* (2013.01); *G02B 6/0053* (2013.01); *G02B 6/3512* (2013.01); *G06T 11/003* (2013.01); *G01J 2003/423* (2013.01); *G01N 2021/3513* (2013.01); *G02B 5/08* (2013.01); *G02B 6/4215* (2013.01)

(58) Field of Classification Search
USPC ...................................................... 250/338.1
See application file for complete search history.

(56) References Cited

U.S. PATENT DOCUMENTS

| | | | | |
|---|---|---|---|---|
| 2003/0038238 | A1* | 2/2003 | Haeusler | G01N 21/3504 250/339.13 |
| 2013/0003046 | A1* | 1/2013 | Izawa | G01N 21/05 356/51 |
| 2015/0160126 | A1* | 6/2015 | Carangelo | G01N 21/3504 356/437 |
| 2017/0059477 | A1* | 3/2017 | Feitisch | G01N 21/274 |
| 2017/0097274 | A1* | 4/2017 | Thorpe | G01B 21/20 |

OTHER PUBLICATIONS

Webster, C. et al., "Quantum-cascade laser measurements of stratospheric methane and nitrous oxide", Applied Optics, Jan. 20, 2001, pp. 321-326, vol. 40, No. 3.
Joly, L. et al., "Development of a spectrometer using a continuous wave distributed feedback quantum cascade laser operating at room temperature for the simultaneous analysis of N2O and CH4 in the Earth's atmosphere", Applied Optics, Mar. 20, 2008, pp. 1206-1214, vol. 47, No. 9.
Van Neste, C. W. et al., "Standoff Spectroscopy of Surface Adsorbed Chemicals", Analytical Chemistry, Mar. 1, 2009, pp. 1952-1956, vol. 81, No. 5.
Van Neste, C. W. et al., "Standoff Photoacoustic Spectroscopy", Applied Physics Letters, 2008, pp. 234102-1 to 234102-3, vol. 92.
Ferrari, A. et al., "Raman spectroscopy as a versatile tool for studying the properties of graphene", Nature Nanotechnology, Apr. 2013, pp. 235-246, vol. 8.
Es-Sebbar, E. et al., "Absolute nitrogen atom density measurements by two-photon laser-induced fluorescence spectroscopy in atmospheric pressure dielectric barrier discharges of pure nitrogen", Journal of Applied Physics, 2009, pp. 073302-1 to 073302-7, vol. 106.
Cremers, D. et al., "Handbook of Laser-Induced Breakdown Spectroscopy", 2006, pp. 1-283.
Cormack, A., "Representation of a Function by Its Line Integrals, with Some Radiological Applications", Journal of Applied Physics, Sep. 1963, pp. 2722-2727, vol. 34, No. 9.
Kak, A. et al., "Principles of Computerized Tomographic Imaging", 1988, pp. 1-322.
Hanson, P. et al., "A method for experimental heating of intact soil profiles for application to climate change experiments", Global Change Biology, Feb. 2011, pp. 1083-1096, vol. 17, Issue 2.
Sturtevant, C. et al., "Soil moisture control over autumn season methane flux, Arctic Coastal Plain of Alaska", Biogeosciences, Apr. 2012, pp. 1423-1440, vol. 9, Issue 4.
Conway, T. et al., "Atmospheric Carbon Dioxide Dry Air Mole Fractions from the NOAA ESRL Carbon Cycle Cooperative Global Air Sampling Network", 1968-2011, Version: 2012-08-15 ftp://ftp.cmdl.noaa.gov/ccg/co2/flask/month/.
Klenbusch, M., "Measurement of Gaseous Emission Rates from Land Surfaces Using an Emission Isolation Flux Chamber", Environmental Protection Agency, Feb. 1986, pp. 1-58, EPA/600/8-86/008.
Yang, B. et al., "Environmental controls on water use efficiency during severe drought in an Ozark Forest in Missouri, USA", Global Change Biology, 2010, pp. 2252-2271, vol. 16.
Chowdhury, T. et al., "Stoichiometry and temperature sensitivity of methanogenesis and CO2 production from saturated polygonal tundra in Barrow Alaska", Global Change Biology, 2015, pp. 722-737, vol. 21.
Lara, M. et al., "Polygonal tundra geomorphological change in response to warming alters future CO2 and CH4 flux on the Barrow Peninsula", Global Change Biology, 2015, pp. 1634-1651, vol. 21.
Zona, D. et al., "Cold season emissions dominate the Arctic tundra methane budget", Proceedings of the National Academy of Sciences of the USA, Jan. 6, 2016, pp. 40-45, vol. 113, No. 1.
Hartl, A. et al., "2-D reconstruction of atmospheric concentration peaks from horizontal long path DOAS tomographic measurements: parametrisation and geometry within a discrete approach", Atmospheric Chemistry and Physics, 2006, pp. 847-861, vol. 6.
Fischer, M. et al., "Rapid measurements and mapping of tracer gas concentrations in a large indoor space", Atmospheric Environment, 2001, pp. 2837-2844, vol. 35.
"Greenhouse Gas Laser Imaging Tomography Experiment (Green LITE)", http://www.netl.doe.gov/File%20Library/factsheets/project/FE0012574.pdf.
Lange, K. et al., "A Theoretical Study of Some Maximum Likelihood Algorithms for Emission and Transmission Tomography", IEEE Transactions on Medical Imaging, Jun. 2, 1987, pp. 106-114, vol. MI-6, No. 2.
Bingham, P. et al., "Multi-spectral Infrared Computed Tomography", Proceedings, Electronic Imaging Conference, Feb. 14, 2016, pp. 1-5.
Ellingson, W. et al., "Three-dimensional Radiographic Imaging", pp. 1-38.

* cited by examiner

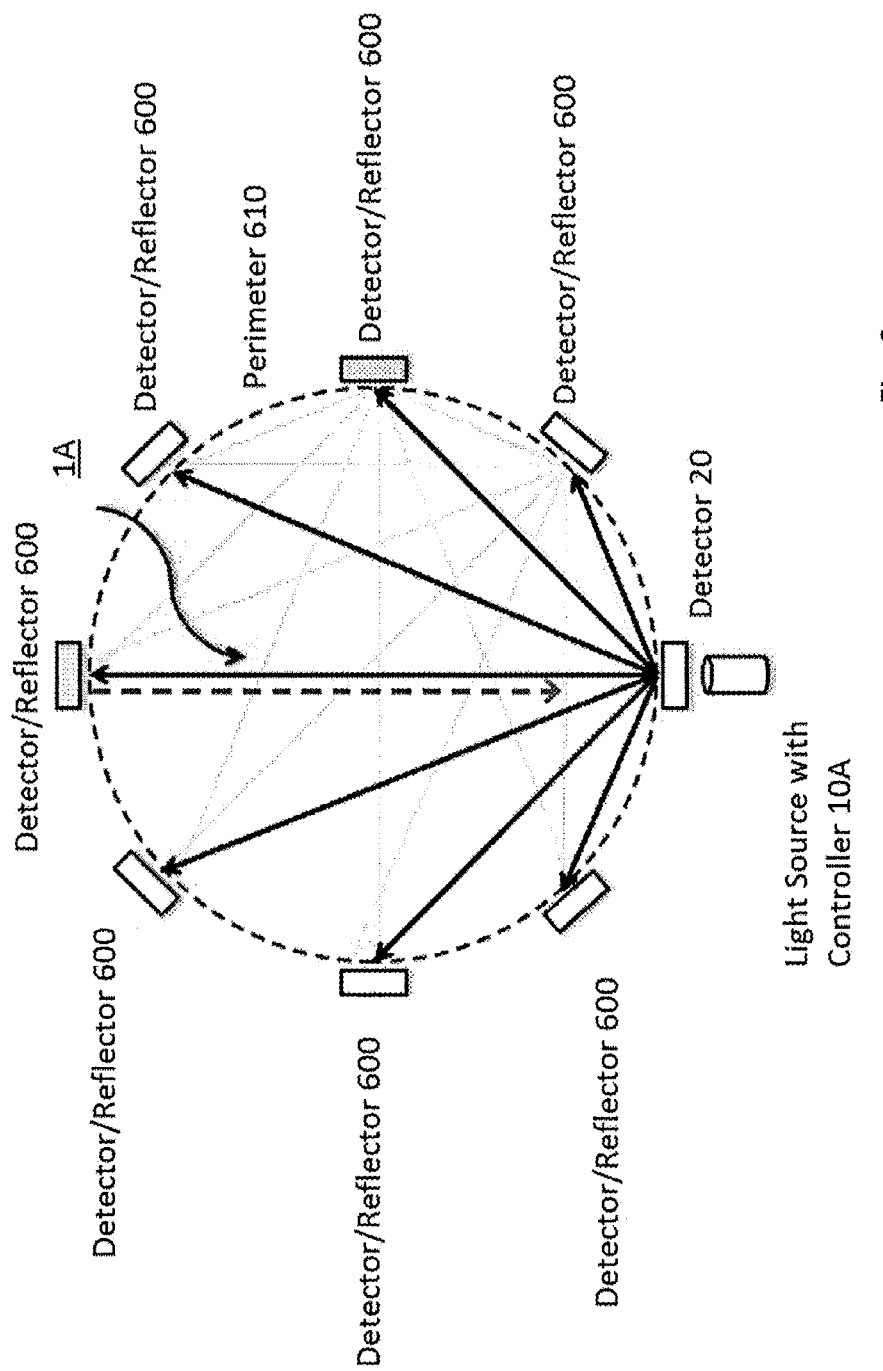

CTIR SPECTROMETER FOR LARGE AREA ASSESSMENT OF GAS EMISSIONS

CROSS-REFERENCE TO RELATED APPLICATIONS

This application claims the benefit of and priority to U.S. Provisional Application Ser. No. 62/330,882 filed May 3, 2016, the contents of which is incorporated herein by reference.

STATEMENT REGARDING FEDERALLY SPONSORED RESEARCH AND DEVELOPMENT

This invention was made with government support under Contract No. DE-AC05-00OR22725 awarded by the U.S. Department of Energy. The government has certain rights in the invention.

FIELD OF THE DISCLOSURE

This disclosure relates to systems, methods and programs for detecting a presence and distribution of gas in an area.

BACKGROUND

The presence of gas can adversely impact the ecosystem and climate and vice versa. For example, arctic tundra is rapidly evolving as permafrost degrades, potentially releasing vast amount of carbon stored in frozen soils. Certain studies, such as, Next Generation Ecosystem Experiment, in the arctic, have been designed to answer questions regarding the effect of permafrost thawing (and the associated changes in landscape, hydrology, soil bio-geochemistry and plant community) on the global climate system. In order to develop a process-rich ecosystem model at the scale of a high-resolution grid, monitoring the chemical environment over large scale is important. This monitoring of chemical information can be both persistent and on-demand. Chemical species such as $CO_2$, $CH_4$, $H_2O$ and perhaps nitrous compounds, need to be monitored as a function of time in terms of quantity and location.

Several attempts have been made for the detection of different chemicals. However, identification of these materials in a real environment remains a challenge. For example, many of the attempts rely on high power lasers that compromise the safety of the operator and bystanders. Additionally, the sensitivity and/or selectively is affected by environmental factors and interferences.

Knowledge of chemicals presence in the ecosystem is also important for natural gas exploration.

SUMMARY

Accordingly, disclosed are systems, methods and programs for determining the presence and distribution of gas emissions.

In an aspect of the disclosure, disclosed is a system for determining a presence and distribution of gas emissions in an area. The system comprises a plurality of light detectors disposed around a perimeter of an area, a light source and one or more processors. The light source is configured to emit light at a plurality of wavelengths towards each of the plurality of light detectors. Each detector receives light at each of the plurality of wavelengths. The one or more processors is configured to receive information representing light intensity detected by each of the plurality of light detectors, respectively at each of the plurality of wavelengths and determine gases present in each path between the light source and a respective detector based on the light intensity detected by the respective detector at each of the plurality of wavelengths and a distribution of the gases.

In an aspect of the disclosure, the system further includes a reflector co-located with at least one detector or separate from each of the plurality of detectors. The reflector is configured to rotate at a preset angle such that the emitted light at each of the plurality of wavelengths is reflected towards each of the other plurality of detectors or each of the plurality of detectors. The rotation forms at least one set of source-reflector-detector light paths. The one or more processors is further configured to receive information representing light intensity detected by each of the plurality of light detectors respectively at each of the plurality of wavelengths directly from the light source and information representing an intensity of reflected light respectively detected at each of the other plurality of detectors or each of the plurality of detectors at each of the plurality of wavelengths, being reflected by the reflector co-located with at least one detector or separate from each of the plurality of detectors, and determine gases present in each respective light path, each light path being light source to a respective detector or light source to respective reflector to respective detector at each of the plurality of wavelengths based on the received information, respectively.

In an aspect of the disclosure, the one or more processors is configured to determine the gases for each voxel within the area. A voxel represents a location within the area on reconstructed images of the area. The reconstructed images contain a plurality of voxels.

In an aspect of the disclosure, the light source is a quantum cascade laser system configured to emit infrared light.

In an aspect of the disclosure, detector(s) can be either fixed in a preset location or located in an unmanned aerial vehicle.

In another aspect of the disclosure, the light source can be either fixed in a preset location or located in another unmanned aerial vehicle.

Also disclosed is a system for determining a presence and distribution of gas emissions in an area. The system comprises a plurality of reflectors, or a plurality of retroreflectors disposed around a perimeter of an area, a light detector disposed on the perimeter of the area, a light source and a processor. The light source is configured to emit light at a plurality of wavelengths towards each of the plurality of reflectors or retroreflectors, whereby for each of the plurality of reflectors or retroreflectors, the light is reflected at each of the plurality of wavelengths to a single light detector. The processor is configured to receive information representing light intensity detected by the detector, respectively at each of the plurality of wavelengths and determine gases present in each path based on the light intensity detected by the detector at each of the plurality of wavelengths.

BRIEF DESCRIPTION OF THE FIGURES

FIG. 6 illustrates a diagram of another system for detecting the presence and distribution of gas emissions in accordance with aspects of the disclosure;

FIG. 16A is reconstructed with both interpolation in a projection space and smoothing filters in a voxel space; FIG. 16B is reconstructed with smoothing filters in the voxel space;

DETAILED DESCRIPTION

Figure 1:
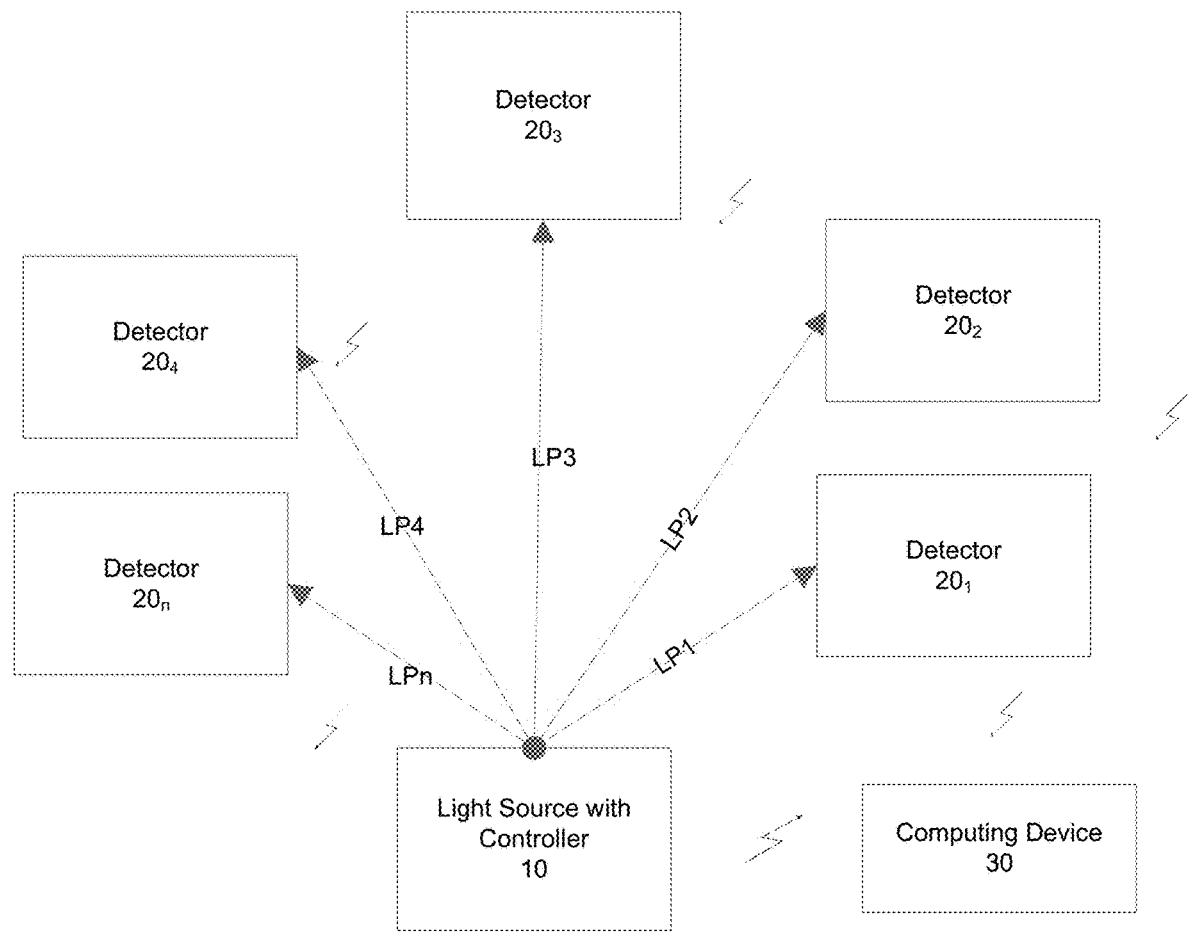
FIG. 1 illustrates a block diagram of a system for detecting the presence and distribution of gas emissions in accordance with aspects of the disclosure.

FIG. 1 illustrates a block diagram of a system 1 for detecting the presence and distribution of gas emissions within a target area ("area of interest") in accordance with aspects of the disclosure. The system 1 comprises a plurality of light detectors 20 and a light source 10 (with controller). The detectors 20 are positions along the perimeter of an area of interest. The area of interest can have a diameter of 1 Km or more. The area of interest may be any position within the atmosphere, such as, but not limited to, the arctic tundra, area above a gas exploration site or the area around a chemical plant.

The detectors 20 may be positioned equi-distant from each other along the perimeter of the area of interest. However, the detectors 20 are not required to be equi-distant from each other. In an aspect of the disclosure, the detectors 20 are positioned at a fixed-known location on the perimeter. The light source with controller 10 is also positioned at a fixed-known location on the perimeter of the area of interest.

In an aspect of the disclosure, the light source with controller 10 is positioned at the same elevation as each of the detectors 20 such that 2-Dimensional maps can be generated. In another aspect of the disclosure, the detectors 20 may be disposed at different elevations such that multiple 2-Dimensional maps (reconstruction) can be generated. In another aspect of the disclosure, the detectors 20 may be disposed at different elevations and be aligned such that a single 2-Dimensional map can be generated.

It is noted that the light source is not necessarily 2-Dimensions but rather is 3-dimensions. Thus, even a 2-Dimensional map effectively provides information for a $3^{rd}$ dimension. Moreover, the 2-Dimensional maps may be aggregated to generated 3-Dimensional maps of the area. In an aspect of the disclosure, each detector 20 is positioned such that there may be a line of sight between each detector and the light source. The light source and each detector $20_{1-n}$ form a source detector pair where the detector $20_{1-n}$ detects the light received from the light source over a respective light path (LP). When light is emitted from the light source, the light is scanned through the area of interest (at a plurality of wavelengths) over multiple light paths ($LP_{1-n}$). In an aspect of the disclosure, as described further herein, the light can be rotated such that light is emitted to each detector. One pass of light across each detector creates a single projection (multiple paths) which may be used to reconstruct a 2-Dimensional cross-section image representing attenuation of light caused by absorption by gases in the area of interest.

The area of interest can be regular shaped such as circular or rectangular or an irregular shape.

The system 1 further includes a computing device 30. The computing device 30 receives information regarding the intensity of light received by each detector $20_{1-n}$ (at each wavelength) and determines the transmittance of the light over the wavelengths. The computing device 30 examines the transmittance (or attenuation) to determine the presence and distribution of gas emissions in the area of interest. The determination of the presence and distribution of gas emissions will be described in detail later.

In an aspect of the disclosure, the computing device 30 receives the information regarding the intensity of detected light wirelessly, either on a continuous basis or in a batch. In another aspect of the disclosure, the information regarding the intensity of the detected light is stored in each detector and an operator retrieves the information from each detector and uploads the same into the computing device 30. Additionally, the computing device 30 receives information regarding the intensity of the light emitted by the light source. For example, the light source with controller 10 may wirelessly transmit the intensity information to the computing device 30. In another aspect of the disclosure, the intensity information of the emitted light is preset and stored in a memory of the computing device 30.

FIG. 1 depicts the computing device 30 separate from the light source with controller 10, however, the computing device 30 can be integrated into the same.

Figure 2:
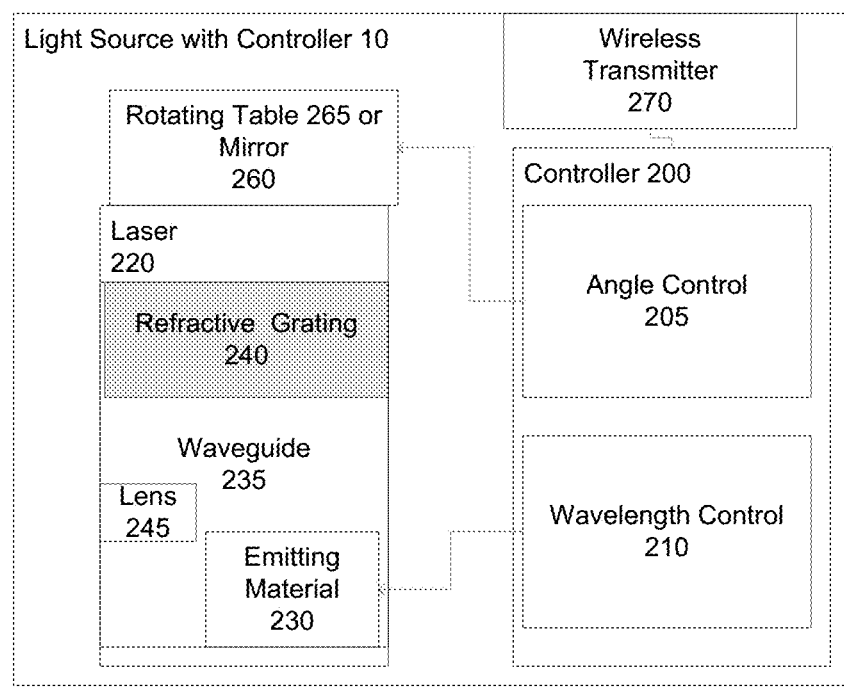
FIG. 2 illustrates a block diagram of a light source with a controller in accordance with aspects of the disclosure.

FIG. 2 illustrates a block diagram of a light source with a controller in accordance with aspects of the disclosure. The light source with controller 10 may comprise a laser 220 and controller 200. The laser 220 is tunable. The laser 220 may include an emitting material 230, a waveguide 235 and lens 245. In an aspect of the disclosure, the laser 220 is configured to emit light in the infrared range. For example, the laser 220 may be a single source containing one or multiple quantum cascade laser (QCL) modules.

Figure 19:
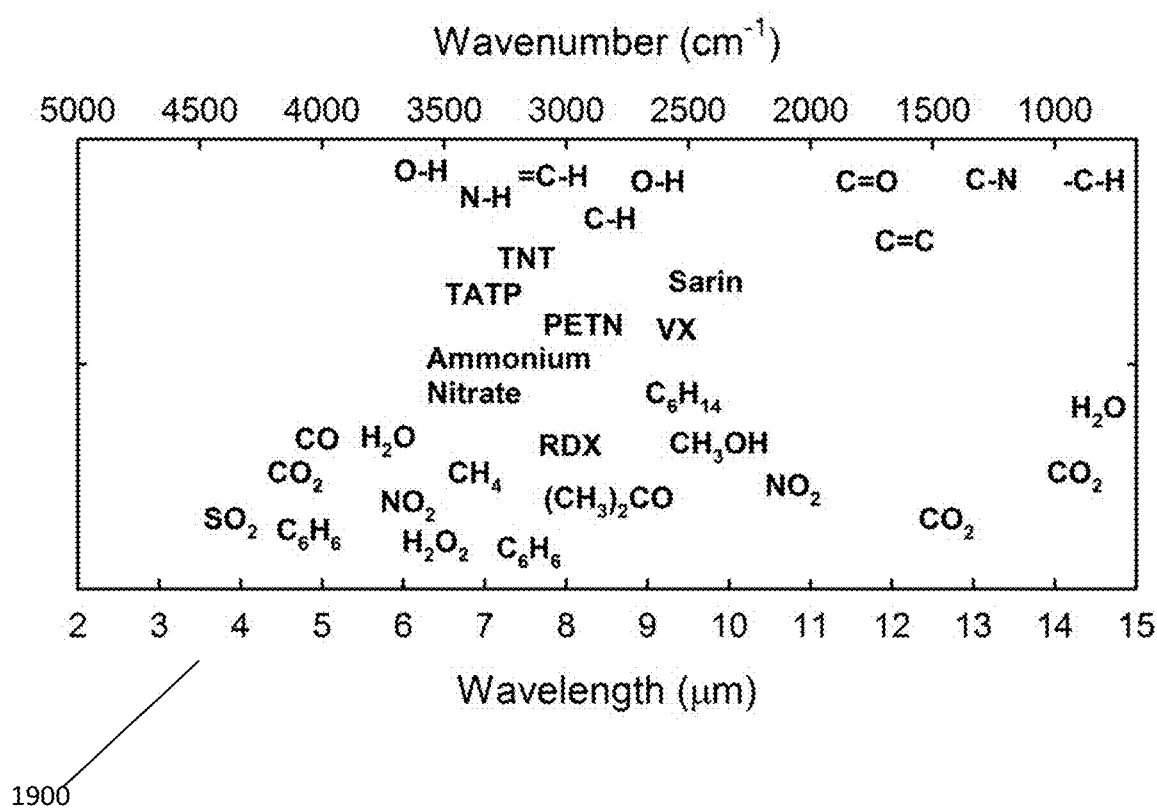
FIG. 19 is a chart showing molecular absorption in the infrared spectrum for different species.

As seen in the chart 1900 in FIG. 19, $CO_2$ has absorption near 4.3 μm and $CH_4$ has absorption near the wavelengths of 3.3 μm and 7.7 μm. The wavelengths of the light source, e.g., QCL may be selected and tuned to be able to detect a variety of chemical species of interest such as, but not limited to $CO_2$, $CH_4$, $N_2O$ and $H_2O$.

For example, the modules are formed of one or more emitting materials and waveguide and may provide a wavelength range from about 3 µm to about 15 µm. For example, for detecting $CO_2$, an optimal choice may include a tunable QCL module centered around 4.3 µm, while for $CH_4$, an optimal choice may includes tunable QCL modules centered around 3.3 µm and/or 7.7 µm.

Illumination in the mid-IR range is suited for measurements over large outdoor areas since mid-IR lasers remain eye-safe at energy levels high enough to measure over long distances, and mid-IR band is also less attenuated by moisture in the air than short wavelength IR bands. A refractive grating 240 may also be disposed over the surface of the waveguide to further selectively emit a specific wavelength. The laser 220 is controlled by controller 200. The Controller 200 is configured to sweep the wavelengths over time (wavelength control 210). For example, the Controller 200 may control the laser 220 to sweep between about 3 µm to about 15 µm in nanometer steps. In an aspect of the disclosure, the step size can be about 2 nm, 5 nm, 10, 25 nm. These step sizes are only by way of example, and other step sizes may be used, as needed. The step size can be preset by an operator. In an aspect of the disclosure, the Controller 200 can control the wavelength emitted based on adjusting the temperature of the emitting material or bias current.

The Controller 200 may also control the angle (angle control 205) of the emitted light. In an aspect of the disclosure, the laser 220 may be attached to a rotating table or a rotating stage 265. When the laser 220 is attached to the rotating table or rotating stage 265, the angle control 205 may include a motor configured to turn gears attached to the rotating table to achieve the specific angles. Since the locations of each of the detectors $20_{1-n}$ is fixed and known, the angles of rotation, such that light can be emitted to each of the detectors, sequentially, is also known and therefore can be preset. The angle control 205 uses the motor to rotate the rotating table 265 at these specific angles to emit the light at each of the detectors. In another aspect of the disclosure, the rotating table or rotating stage is omitted and instead a separate reflector or mirror 260 is used. The angle of the reflector or mirror is changed by the angle controller 205 in a similar manner. For example, a motor can be used to rotate the reflector or mirror. Thus, the combination of the angle control 205 and wavelength control 210 allows the Controller 200 to control the laser 220 to emit a plurality of wavelengths at a respective detector, afterwards rotate the light to another detector and repeat, until all of the wavelengths are respectively emitted towards each detector.

In an aspect of the disclosure, the Controller 200 may also include a clock or timer and a storage device (not shown). The storage device may include a table recording the time of emission of the specific wavelength and angle of the light such that the computing device 30 can correlate the intensity information with the emitted wavelength and received intensity information of a detector. The time/wavelength information can be periodically transmitted wirelessly from the light source with controller 10 to the computing device 30 via the wireless transmitter 270.

Figure 3:
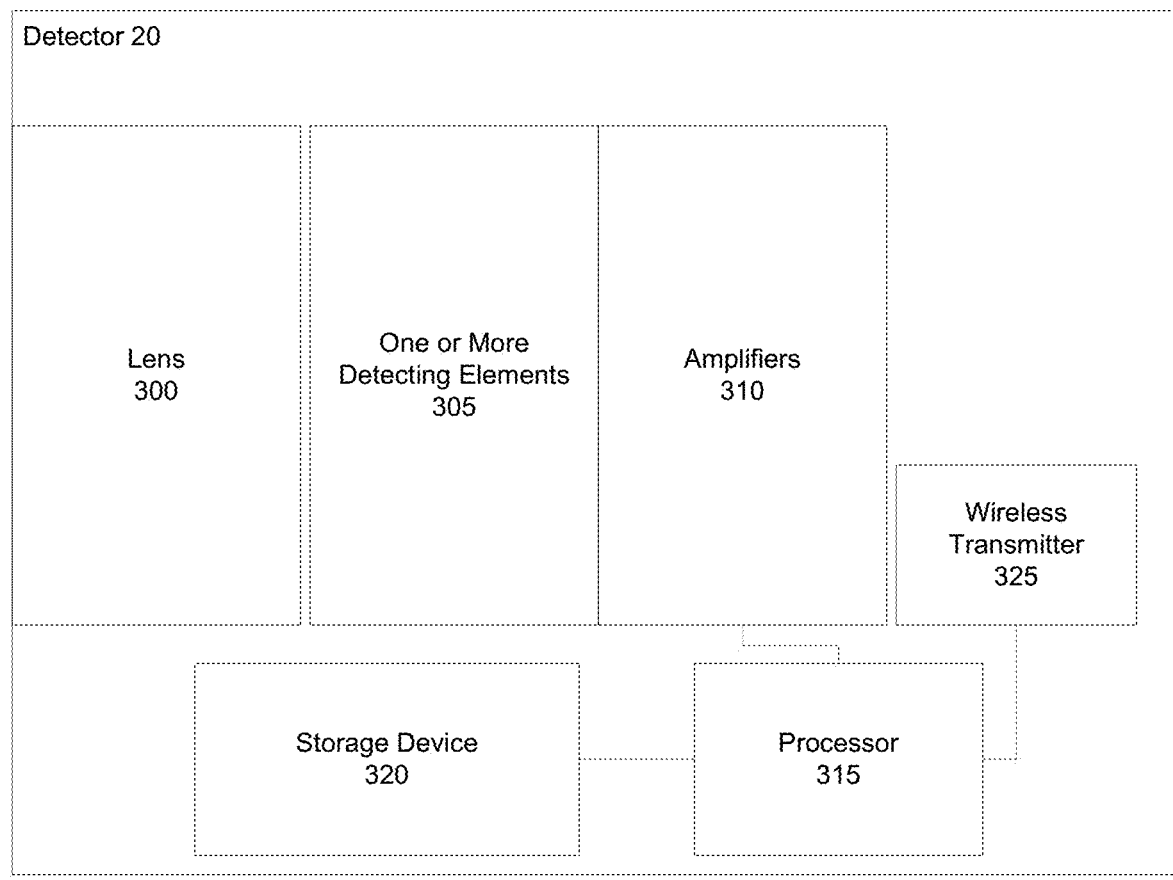
FIG. 3 illustrates a block diagram of a detector in accordance with aspects of the disclosure.

FIG. 3 illustrates a high level block diagram of an example of a detector 20 for use in the system 1. The detector 20 can be any light detector such as, but not limited to, bolometer, an infrared camera, photodiode, photoresistor, photovoltaic, thermopile and photoconductive detector. By way of an example, the detector 20 can be a mercury cadmium telluride (MCT) detector.

A single detector 10 may include one or more of the above detecting components or elements 305. The detecting components 305 have different spectral response characteristics, e.g., photosensitivity. Using one or more detecting components 205 in the detector 20 allows the detector to be selectively tuned to detect wavelengths within a desired region. In an aspect of the disclosure, the detector 20 may be configured to detect light emitted from about 3 µm to about 15 µm. However, other wavelengths may be emitted and detected, as needed. The detector 20 may include lens 300 and/or mirrors to focus the light onto the one or more detecting elements 305.

The detector 20 may also include amplifier(s) 310 for amplifying the electrical response(s) of the one or more detecting elements 305 (if needed). The detector 20 may also include a Processor 315. The Processor 315 is electrically coupled to the one or more detecting elements 305. The Processor 315 causes the electrical response of the one or more detecting elements to be store in a storage device 320. The Processor 315 may also include a clock or timer and record the time of the detection. This will further enable the computing device 30 to correlate the detected values with the (emitted and detected) wavelength. In another aspect of the disclosure, the Processor 315 can record in the storage device 320 which of the one or more detecting elements 305 exhibits an electrical response.

In an aspect of the disclosure, the Processor 315 examines values of electronic response, e.g., current or voltage, and based on the known spectral response, determines the detected intensity of the light (at a wavelength). The Processor 315 may then cause a wireless transmitter 325 to transmit the intensity. In another aspect of the disclosure, the Processor 315 may cause the wireless transmitter to transmit the electronic response and time information to the computing device 30 (and the computing device determines the intensity). The electronic response and time information or intensity is ("intensity information").

Figure 4:
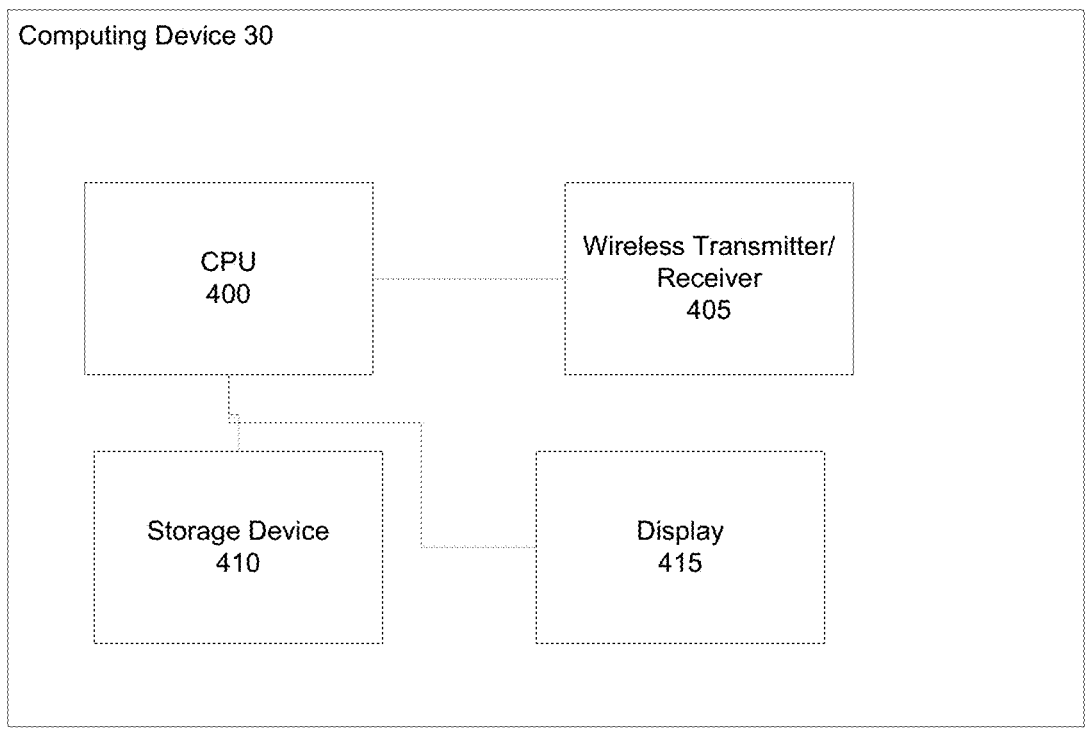
FIG. 4 illustrates a block diagram of a computing device in accordance with aspects of the disclosure.

FIG. 4 illustrates a block diagram of a computing device 30 used in the system 1. The computing device 30 may include a central processing unit (CPU) 400, a wireless transmitter/receiver 405, a storage device 410 and a display 415. The storage device may be, but not limited to, RAM, ROM and persistent storage (not shown in the figures). In an aspect of the disclosure, the CPU 400 can be configured to execute one or more programs stored in a computer readable storage device such as storage device 410. The computer readable storage device can be RAM, persistent storage or removable storage. A storage device is any piece of hardware that is capable of storing information, such as, for example without limitation, data, programs, instructions, program code, and/or other suitable information, either on a temporary basis and/or a permanent basis.

The computing device 30 receives via the wireless transmitter/receiver 405 intensity information from each of the detectors 20 and stores the same in the storage device 410. Each light ray or ray of the projection contains an integrated sample of the atmospheric gas between the light source and the respective detector 20 for a range of wavelengths used in the sweep. For each wavelength, the measured attenuation of each light path is:

$$I(\lambda)=I_o(\lambda)\exp(-\Sigma_i \mu_i(\lambda)\rho_i l_i) \quad (1)$$

where $I(\lambda)$ is the measured intensity, $I_o(\lambda)$ is the transmitted intensity of the emitted light, $\mu_i$ is the absorption cross-section of the gas at wavelength $\lambda$, $\rho_i$, is the gas density and $l_i$ is the path length of the ray through the gas, and I is the index of gas mixtures along the path.

As such, the system 1 is able to obtain information regarding the presence and distribution, e.g., which ray was attenuated, of gas emission along the light paths between the light source 10 and each detector 20 based on equation 1.

Figure 5A:
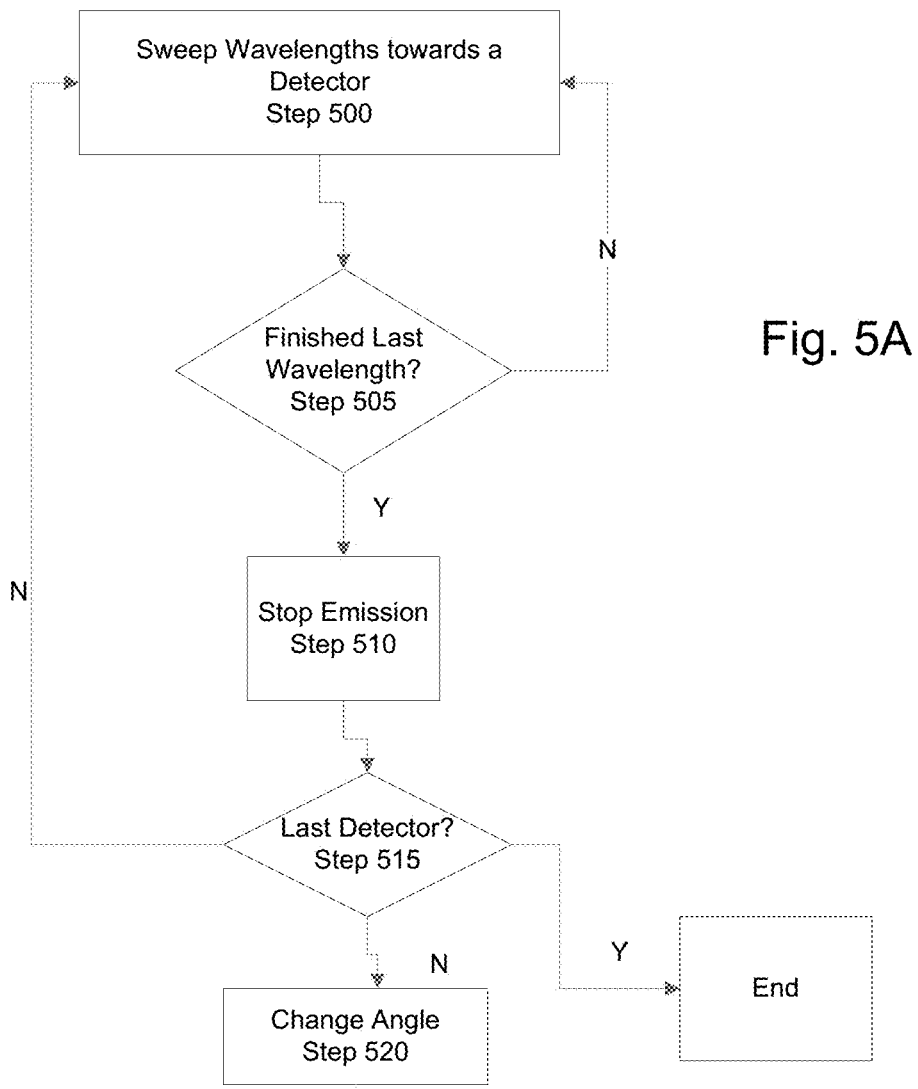
FIG. 5A illustrates a flow chart of a method for controlling the light source in accordance with aspects of the disclosure.

FIG. 5A illustrates a flow chart of a method for controlling the light source is accordance with aspects of the disclosure. At step 500, the Controller 200 (wavelength control 210) sweeps the wavelength of the laser from a minimum wavelength Wmin to a maximum wavelength Wmax at the preset step size towards the first detector $20_1$. For example, the step size is 10 nm over a predetermined time. Thus, the light source is aligned with the first detector $20_1$. The light source is maintained in alignment with the first detector $20_1$ until all of the wavelengths between Wmin and Wmax are emitted (through the step size). Optionally, the Controller 200 records the time of emission of each wavelength indexed by wavelength. At step 505, the Controller 200 determines if the sweep is finished, e.g., Wmax. In an aspect of the disclosure, the Controller 200 may use time in this determination. For example, based on the time per step, the step size and the difference between Wmin and Wmax, the Controller 200 may determine the expected time to complete one sweep. Thus, the Controller 200 may determine that the sweep time equals the expected sweep time as an indicator that the Wmax has been emitted. In another aspect of the disclosure, the Controller 200 may use direct knowledge of the wavelength emitted by the wavelength control 210 to determine whether the sweep is finished.

If the sweep is finished ("Y"), the wavelength control 210 may stop the laser 220 from emitting light and the angle control 205 controls the light to change angle by a specific amount such that the light can be emitted towards the second detector $20_2$. Once the angle of the light source has changed by the specific amount, the wavelength control 210 (of the controller 200) starts the wavelength sweep for the second detector $20_2$ (returns to step 500). The process is repeated for each detector $20_{1-n}$ in the system 1. At step 520, the Controller 200 determines if the light source has been emitted to each detector $20_{1-n}$. If "Y", the process ends.

Figure 5B:
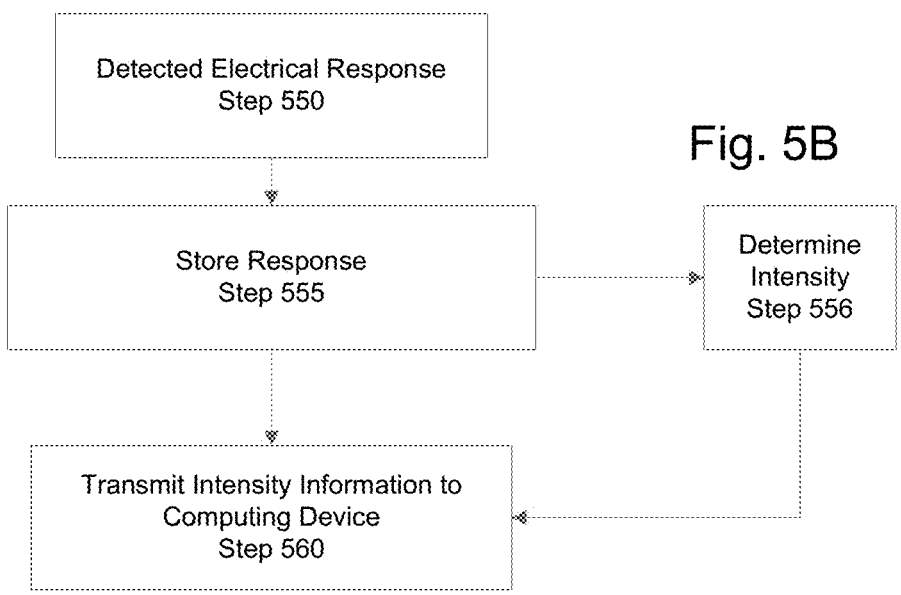
FIG. 5B illustrates a flow chart of a method for detecting light intensity in accordance with aspects of the disclosure.

FIG. 5B illustrates a flow chart of a method for detecting light intensity in accordance with aspects of the disclosure. At step 550, the Processor 315 determines if an electrical response has occurred in the one or more detecting elements. If "Y", the Processor 315 stores the electrical response in the storage device 320. The Processor 315 may also store a time of the electrical response which is used to correlate the wavelength. Based on the known spectral response of the one or more detecting elements, the Processor 315 may determine the intensity of the light received using the electrical response at step 556 and cause the wireless transmitter 325 to transmit the intensity of the light received as intensity information to the computing device 30 at step 560. In another aspect of the disclosure, the Processor 315 may cause the wireless transmitter 325 to transmit the raw electrical response and time information to the computing device 30 at step 560.

FIG. 6 illustrates a diagram of an example of another system 1A for detecting the presence of gas emissions within an area of interest in accordance with aspects of the disclosure. System 1A is similar to system 1 except that system 1 may also include a reflector co-located with at least one detector and that the detectors/reflectors can be rotated for alignment, e.g., creating different optical paths. In another aspect of the disclosure, the reflector can be separate from the detector.

Additionally, in an aspect of the disclosure, instead of reflectors, retroreflectors can be used to reflect light back to the source. A Detector/Reflector is identified in FIG. 6 as "600". In the example depicted in FIG. 6, a detector 20 is also located in the same position as the Light Source with Controller 10A. The Detectors/Reflectors 600 are located along the perimeter 610 of the area of interest. The system 1A created multiple projections or scans of the area of interest by changing the emission angle of the light from the light source, angles of the detectors and angles of the reflectors or retroreflectors. For example, there are a series of LPs directly from the light source with Controller 10A (identified by the darker line in FIG. 6 collectively represent a single scan or projection). A single projection includes multiple light paths or rays. Additionally, there are multiple series of reflected light paths (RLPs) between a reflector and another detector. The RLPs are shown in the lighter lines in FIG. 6. For simplicity of the drawing, only two sets of reflected light paths are shown in FIG. 6. However, the number of different sets of reflected light paths would equal the number of reflectors deployed in the system 1A.

Advantageously, in the system 1A, different angles and sets of light paths can be created from a single light source 10A by optically translating the same through the reflectors. For example, the light source is traversed around the perimeter 610 of the system 1A to collected multiple projections and light paths. By incorporated reflector/mirrors that can be controlled to specific angles, it is possible to send the source around at least 180 degrees of the perimeter 610 without having to relocate or replicate an additional light source.

Figure 7:
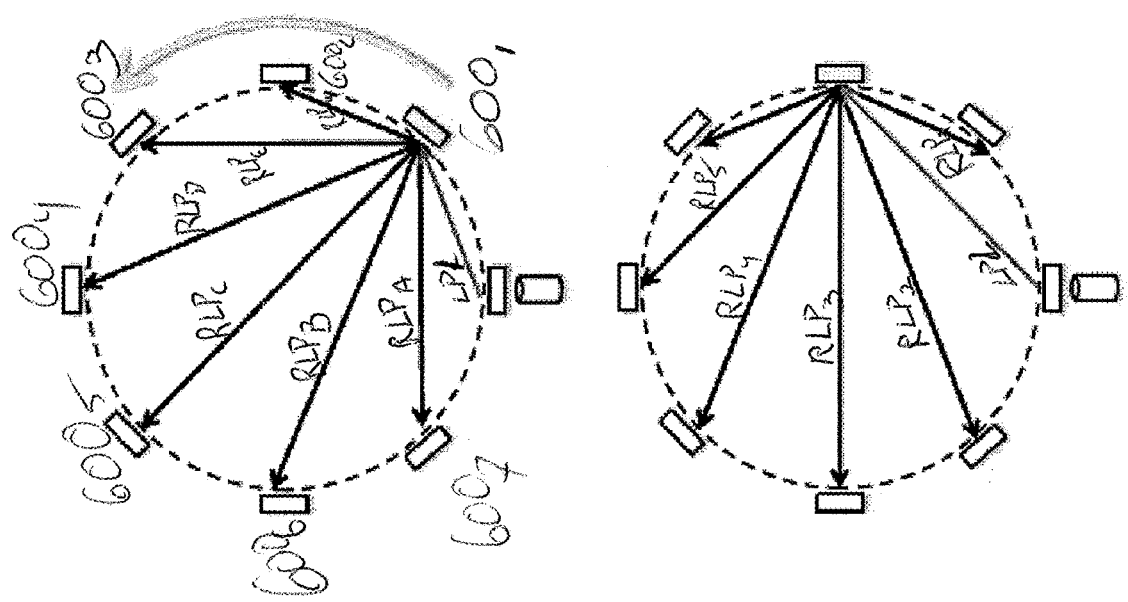
FIG. 7 illustrates a diagram of two rotations of light paths, e.g., two projections.

FIG. 7 shows an example of two sets of light paths. The sets of paths include a direct light path of the light source LP2 (bottom) and LP1 (top) and reflected light paths $RLP_1$-$RLP_6$ (bottom) and $RLP_A$-$RLP_F$ (top). The curved arrow reflects the direction of rotation of the light source from the light source with Controller 10A. Each stop in the rotation creates a different projection containing multiple light paths or rays.

FIG. 6 also illustrates a reflected light path back to a detector co-located with the light source with controller 10A (dashed line).

The multiple sets of light paths (direct source-detector and a path comprising a combination of direct and reflected, e.g., source-reflector-detector) are used to reconstruct the spectral information at every spatial position (in a reconstruction space or voxel space) within the area of interest by using computer topographic techniques. The intensity of light received at a detector/reflector which is reflected through one or more reflecting elements is impacted by the gas absorption along both the LP and each RLP, e.g., attenuation.

For example, the multiple projections are used to reconstruct images representative the attenuations of light at each of the plurality of wavelengths and spectral attenuations at each voxel in the reconstruction or voxel space using computer tomography (CT) techniques to recover the gas emissions and concentrations at all spatial positions, e.g., voxels. In an aspect of the disclosure, a voxel represents a location within the area of interest, such that a plurality of voxels on an image represents the area of interest.

In an aspect of the disclosure, the angle of each detector/reflector 600 can be independently controlled by a central controller interacting with motors co-located with the detector/reflector. A central control enables a global knowledge of the angle for each of the detectors/reflectors 600. In an aspect of the disclosure, the central controller can be located within the Light Source with Controller or a separate computing device.

Figure 8:
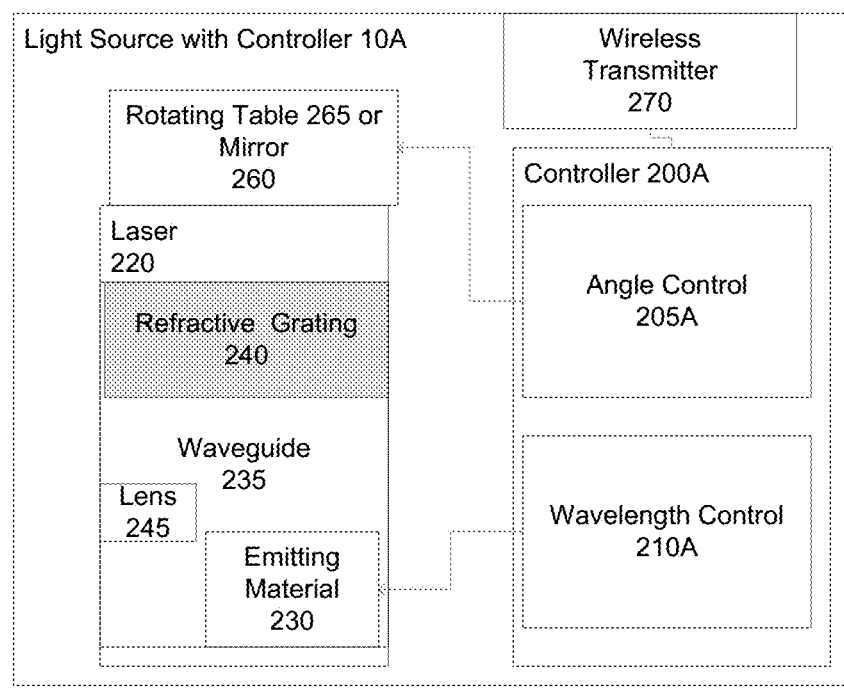
FIG. 8 illustrates a block diagram of another light source with a controller in accordance with aspects of the disclosure.

FIG. 8 illustrates a block diagram of light source with a controller 10A in accordance with aspects of the disclosure. The light source with a controller 10A is similar as the light source with a controller 10 and the same components will not be described again. The light source with a controller 10A includes Controller 200A (instead of Controller 200). Controller 200A controls the angle of the light source, angles of the detectors/reflectors and wavelength emitted by the laser.

Figure 9:
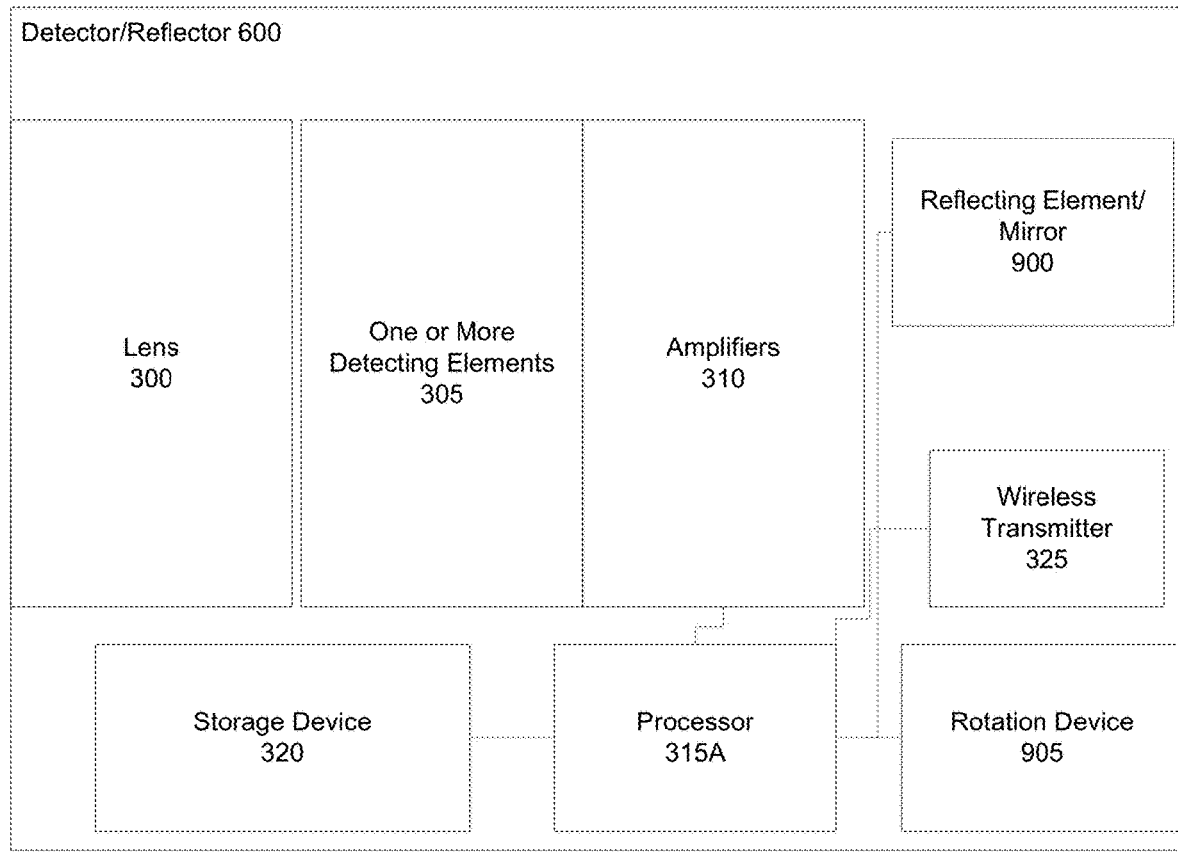
FIG. 9 illustrates a block diagram of a detector/reflector in accordance with aspects of the disclosure.

FIG. 9 illustrates a block diagram of a detector/reflector 600 in accordance with aspects of the disclosure. Several of the components of the detector/reflector 600 are the same as detector 20 and therefore will not be described again. The detector/reflector 600 further includes a reflecting element 900 such as a mirror configured to reflect the light emitted from the laser 220 to other detectors. The reflecting element 900 is rotatably attached to the detector. The detector/reflector 600 further includes a rotation device 905. The rotation device 905 may be configured to rotate the detector to align with the reflector (e.g., reflected light) associated with another detector to create the line of sight. The alignment is based on the angle of incidence and reflection. The rotation device 905 is coupled to the Processor 315A. The rotation device may be a motor in communication with gears for a rotating stage or table. The Processor 315A receives angle commands from the angle control 205A in the light source with controller 10A and causes the reflecting element 900 and rotation device 905 to respectively change the angle of the detector and reflecting element 900, respectively.

Therefore, the angle of the detector and the angle of the reflecting element 900 can be independently controlled.

Figure 10:
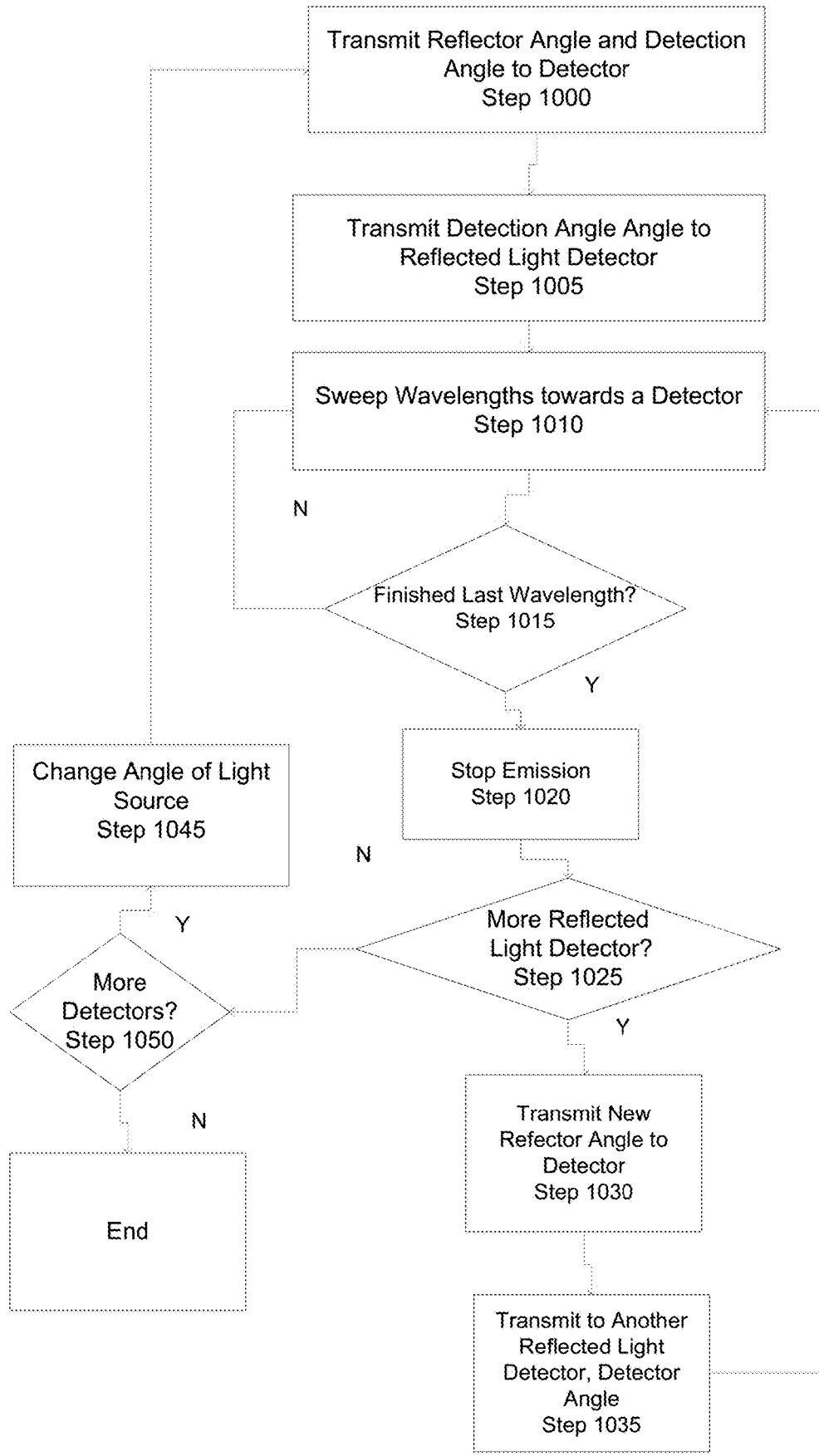
FIG. 10 illustrates a flow chart for a controller in accordance with aspects of the disclosure.

The following description will use the light paths depicted in FIG. 7 as reference for the control of the light source with Controller 10A and detector/reflectors 600 to emit and detect light for multiple projections and sets of light paths along with the flow chart illustrated in FIG. 10.

In order to create LP1 and $RLP_A$, the detecting elements of the detector/reflector $600_1$ needed to be aligned with the laser 220, while the reflecting element 900 needed to be aligned such that the reflected light is emitted towards detector/reflector $600_7$, e.g., the detecting elements of detector/reflector $600_7$. In an aspect of the disclosure, the Controller 200A includes a storage device having a list of angles for each of the detector/reflector combinations, representing the angles needed for line of sight for each of the potential light paths (LPs and RLPs). The angle control 205A retrieves the reflector angle and detection angle needed for the LP1 and $RLP_A$ and transmits the same to detector/reflector $600_1$ using the wireless transmitter 270 at step 1000. Additionally, the angle control 205A retrieves the detection angle for detector $600_7$ and transmits the same to detector/reflector $600_7$ using the wireless transmitter 270 at step 1005. Upon receive of the reflector angle and detection angle, the Processor 315A (of detector/reflector $600_1$) controls both the reflecting element 900 and rotation device 905 based on the received angle information. Specifically, the Processor 315A causes the detector (lens and one or more detecting elements 305) to align with the laser 220 and the reflecting element 900 such that the reflection of the light aligns with detector/reflector $600_7$. Similarly, the processor 315A of the detector $600_7$ causes the detector (lens and one or more detecting elements 305) to align the expected reflection from the reflecting element 900 of the detector/reflector $600_1$.

In the initial run, the light source (laser 220) is in a default position which can be directed toward detector/reflector $600_1$. If the light source is in another position, the angle control 205A will cause the laser 220 to rotate via either the rotating table 265 or mirror 260. Once aligned, the wavelength control 210A will cause the laser 220 to emit light, e.g., sweep the wavelength, as described above, from a minimum wavelength Wmin to a maximum wavelength Wmax at the preset step size at step 1010.

At step 1015, the wavelength control 210A determines if the sweep is finished using either a time threshold or wavelength. If the sweep is finished ("Y"), the wavelength control 210A may stop the laser 220 from emitting light (step 1020), otherwise the sweep continues.

At step 1025, the angle control 205A determines if there are more reflected light detectors, e.g., $600_6$-$600_2$. In an aspect of the disclosure, the controller 200A may include a storage device having an order for the reflected light detector(s) and light detector(s). If there are more reflected light detectors, the detector and reflectors (reflecting element 900) need to be aligned to create $RLP_B$. The angle control 205A retrieves the reflector angle for $RLP_B$ and transmits the same to detector/reflector $600_1$ using the wireless transmitter 270 at step 1030. Additionally, the angle control 205A retrieves the detection angle for detector $600_6$ and transmits the same to detector/reflector $600_6$ using the wireless transmitter 270 at step 1035 (detector $600_6$ is the another reflected light detector). Upon receipt of the reflector angle, the Processor 315A (in detector/reflector $600_1$) causes the reflecting element 900 to rotate while keeping the detector in the same angle (as it is already aligned). Similarly, the processor 315A of the detector $600_6$ causes the detector (lens and one or more detecting elements 305) to align with the expected reflected light from reflecting element 900 of the detector/reflector $600_1$.

Once aligned, Steps 1010-1020 are repeated for the new reflected light path. The determination of additional reflected light detectors is also repeated until no reflected light detector remains.

When no reflected light detectors remain, e.g., "N" at step 1025, the angle control 205 determines if there are more detectors (of the direct light from the laser) remaining at step 1040. In an aspect of the disclosure, this determination is based on prestored information in a storage device in the controller 200A. In the example above, the remaining light detectors include $600_2$-$600_7$. At step 1030, the angle control 205A changes the angle of the light source, e.g., laser 220, by rotating either the rotating table 265 or mirror 260 at step 1045. The light is now directed at detector/reflector $600_2$ as shown in the bottom of FIG. 7 (LP2). Steps 1000-1045 are repeated in the manner as described above forming $RLPS_1$-$RLP_6$.

In another aspect of the disclosure, instead of the above angle control, each reflector and detector may include a constantly rotating or spinning mirror or detecting element. Each constantly rotating or spinning mirrors or detecting element rotates at a different preset rotating speed. Since each rotating speed is preset, the mirrors/detectors will align (line of sight) at known times. Therefore, light detected from the aligned mirrors and detectors may be correlated in time such that the source-detector or source-reflector-detector path is known.

Once the intensity of the light is detected by each of the detectors (either directly or reflected), the light from the laser 220 is stopped.

The detection of light emitted from the laser has been described above and will not be described again (except for the movement of the detectors and reflecting elements).

As illustrated in FIGS. 6 and 7, the reflectors are collocated with detectors. In another aspect of the disclosure, the reflectors are placed in a known-fixed, and separate location from the detectors. In another aspect of the disclosure, a detector and reflector alternate along the perimeter. In another aspect of the disclosure, the reflectors or retroreflectors may be replaced by scattering points along the beam path.

As described above, equation 1 may be used to determine different gases presence along a specific path or ray, however, the goal of using CT is to recover gas density for gas i at each spatial location (x,y), e.g., $\rho_i(x, y)$ (which is displayed as a voxel on a display). The light path referred to in equation 1 is either a light path from a light source to detector (source-detector) or a combined light path from light source to reflector and reflector to detector (source-reflector-detector).

The computing device 30 (not shown in FIGS. 6 and 7) receives the detection information from the detectors/reflectors 600. The computing device 30 reconstructs the 2-dimensional images indicating attenuation at each wavelength within the stepped frequency sweep within the area of interest defined by the perimeter using the detection results. Specifically, the computing device 30 uses CT techniques to obtain $\rho_i(x, y)$.

There are many known CT techniques which may be used by the computing device 30 for reconstructing the images including iterative reconstruction methods such as, but not limited to, maximum likelihood expectation maximization (MLEM), simultaneous iterative reconstruction technique (SIRT), algebraic reconstruction technique (ART) and model based iterative reconstruction (MBIR). Alternatively, the computing device may use a filtered-back projection reconstruction but non-uniformity of the measurements resulting from the unique sampling geometry may cause significant artifacts. The reconstruction technique must account for non-uniform setup, losses in data due to malfunctions in the field, missing data due to blockages along a light path, due to trees, structures or other debris and other non-standard projection paths.

When an iterative reconstruction method is used, a system model that accounts for the unique scanning geometry identified above needs to be generated.

Moreover, any iterative reconstruction method including those listed above may also be adjusted by adding one or more steps such as interpolation and filtering.

Figure 20:
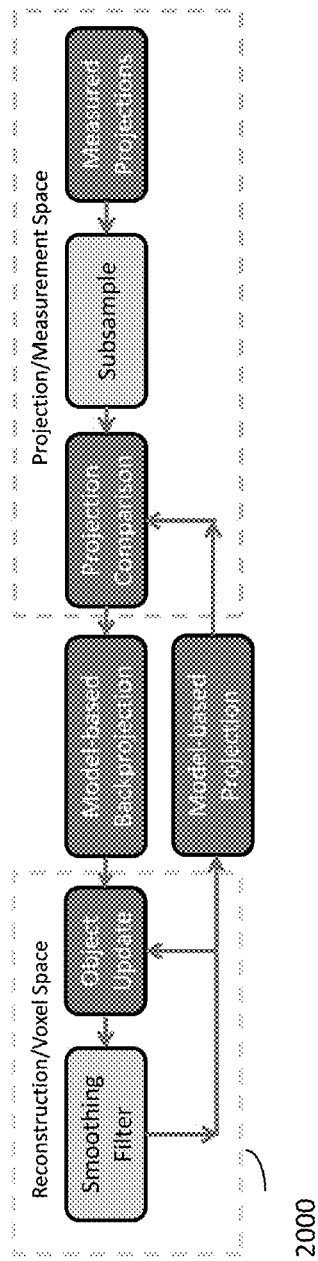
FIG. 20 shows a modified iterative reconstruction method in accordance with aspects of the disclosure which may be used by the computing device for reconstruction.

In a conventional iterative reconstruction method, the measured projections are compared with model-based projections. However, in the modified iterative reconstruction method 2000 (as shown in FIG. 20) in accordance with aspects of the disclosure, prior to comparison, additional rays (also referred to as paths or pixels) for each projection are created to increase the number of rays used for the reconstruction (Subsample). The interpolation assumes that a gas distribution is smooth.

Accordingly, based on this assumption, additional rays are generated through interpolation to increase a number of rays (pixels) in each projection. The number of pixels in each projection equals the number of rays or light paths. The interpolation is also referred to as projection space interpolation. To obtain a smooth reconstruction containing smaller voxels than can be computed by the original set of detection rays (paths), X number of rays (pixels) between each detected ray (pixel) in a single projection is interpolated between neighboring ray (pixel) measurements. Increasing the number of interpolated rays will allow the reconstructed 2-Dimensional map or slice to contain more voxels but smooths the distribution due to the interpolation. The interpolation is repeated for each projection.

The number of rays (pixels) interpolated depends on a desired resolution of the reconstruction. For example, five rays (pixel) positions between each measured ray (pixel) may be used. Linear interpolation between two pixels is based on angular distance. In a circular geometry, the cord through the circle that represents the distance between source and detector varies quickly as the detectors approach the source around the circle. To account for the path length change in the projection interpolation, pixel values on either side of the pixel to be interpolated are normalized (weighted) by the path length for those rays. In an aspect of the disclosure, normalization may be achieved by calculating the total cross section for each path (ray) ($-\log(I/I_0)$), dividing total cross section by the length of the rays to get an average cross section, interpolating between the average cross sections based on angular distance between the pixels and the new ray, multiplying by the ray length for the new interpolated position, and finally converting back to intensity.

The measurements are compared with a model based forward projection of current object results. The comparison than back projected and subsequently used to update the object for the next iteration.

The initial value of the model for the model-based forward projection is generated using the above-described system model (which accounts for scanning geometry). In an aspect of the disclosure, the initial value of the model may assume that no gas emissions are present in the area.

Once the model (model-based forward projection) is created, it is compared with the projection data (including detected and interpolated) (projection comparison). For example, when a a maximum likelihood expectation maximization (MLEM) algorithm is used as the iterative reconstruction method, MLEM uses a division for the comparison.

The model-based back projection is the inverse of the model-based forward projection. The model-based forward projection is updated (Object Update). For example, when the MLEM algorithm is used, a multiplication is used for the update.

Prior to updating the model-based forward projection, a smooth distribution can be forced in the reconstruction space or voxel space using a smoothing filter for each iteration of the reconstruction (smoothing filter). For example, a 3×3 mean filter may be applied to the voxel space. In another aspect of the disclosure, depending on the number of rays (pixels) in the detected projections, the interpolation in the projection space may be omitted (e.g., using smoothing filters without subsample (interpolation)). In another aspect of the disclosure, depending on the number of rays (pixels) in the detected projections, the smoothing filters in the voxel space may be omitted (e.g., using interpolation in the projection space without filtering in the voxel space).

In an aspect of the disclosure, using method 2000, the computing device 30 may generate multiple reconstructed images of the area having a plurality of voxels. Each image represents the attenuation for a specific wavelength (wavelength bin) at each voxel within the area (the above method being repeated for each wavelength). Multiple reconstructed images may then be aggregated to create an attenuation spectrum (or transmittance spectrum) for each voxel. The computing device 30 subsequently compares the generated attenuation spectrum from each voxel with spectral absorption (attenuation) for specific gases and determines the presence and distribution of the gas within the area of interest based on the comparison. Further, the magnitude of the attenuation (or transmittance) (at each position or voxel and at each wavelength), e.g., peak, is proportional to the concentration.

Figure 11A:
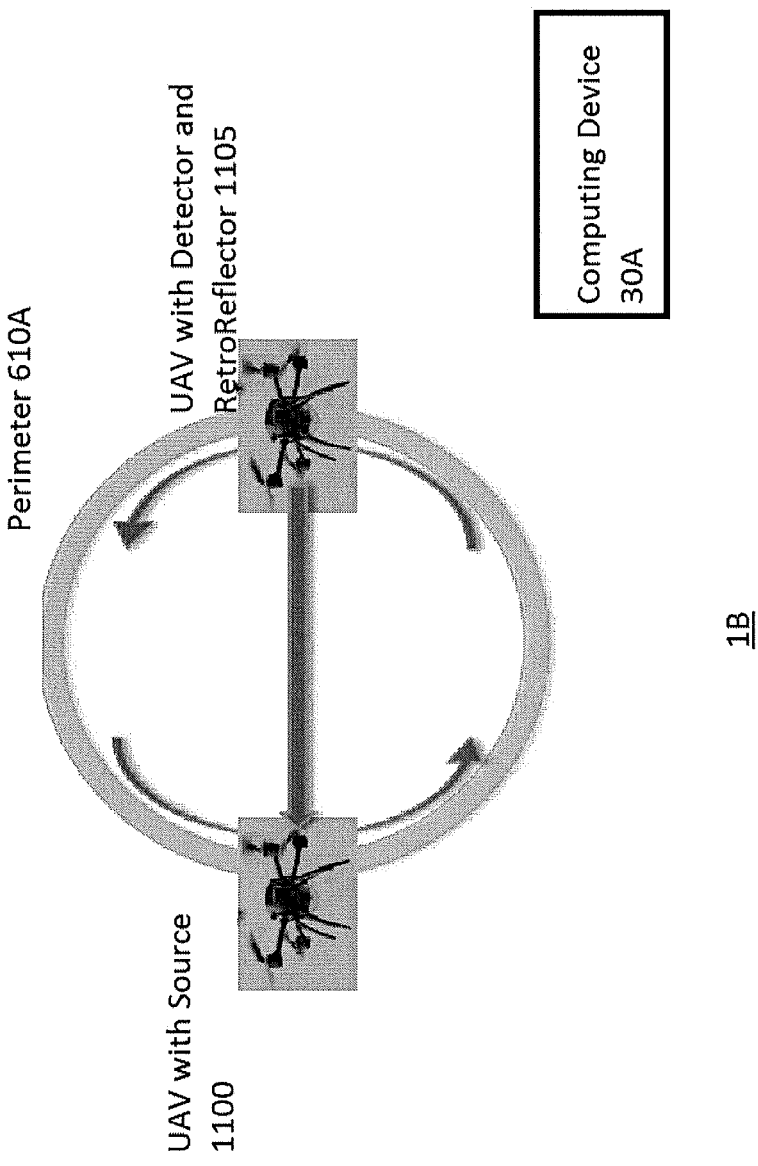
FIGS. 11A and 11B illustrate diagrams of another system for detecting the presence and distribution of gas emissions in accordance with aspects of the disclosure where the light source and detector are attached to unmanned aerial vehicles (UAV)

FIG. 11A depicts another system 1B for determining the presence of gas emissions in accordance with aspects of the disclosure. The difference between the systems 1 and 1A and system 1B is that both the light source and detector move around the perimeter 610A of the area of interest. In system 1B, a light source, e.g., QCL, is installed or mounted to an unmanned aerial vehicle (UAL) (identified in FIG. 11A as 1100). A detector is also installed or mounted to another UAL (identified in FIG. 11A is 1105). Additionally, in an aspect of the disclosure, a retroreflector may also be installed or mounted to the UAV having the detector 1105. When a retroreflector in included in 1105, UAL 1100 also includes a detector. When FIG. 11A only depicts one UAV having a detector/reflector, multiple UAVs may also include detectors.

The UALs 1100/1105 are remotely controlled by a Computing Device 30A. Computing Device 30A is similar to the computing device 30 in that it including a CPU, memory, and display. The Computing Device 30A may transmit and receive information. For example, the computing device 30A transmits positioning commands to the UALs 1100/1105 and receive information related to the intensity of light detected. Computing Device 30A also remotely controls the light emitted from the laser and the angle of the laser (via the orientation of the UAV).

The curved arrows in FIG. 11A represent the respective motion of the UAVs 1100/1105 around the perimeter. The arrow 1110 from UAV 1105 to UAV 1100 represents light reflected back from the retroreflector.

Figure 11B:
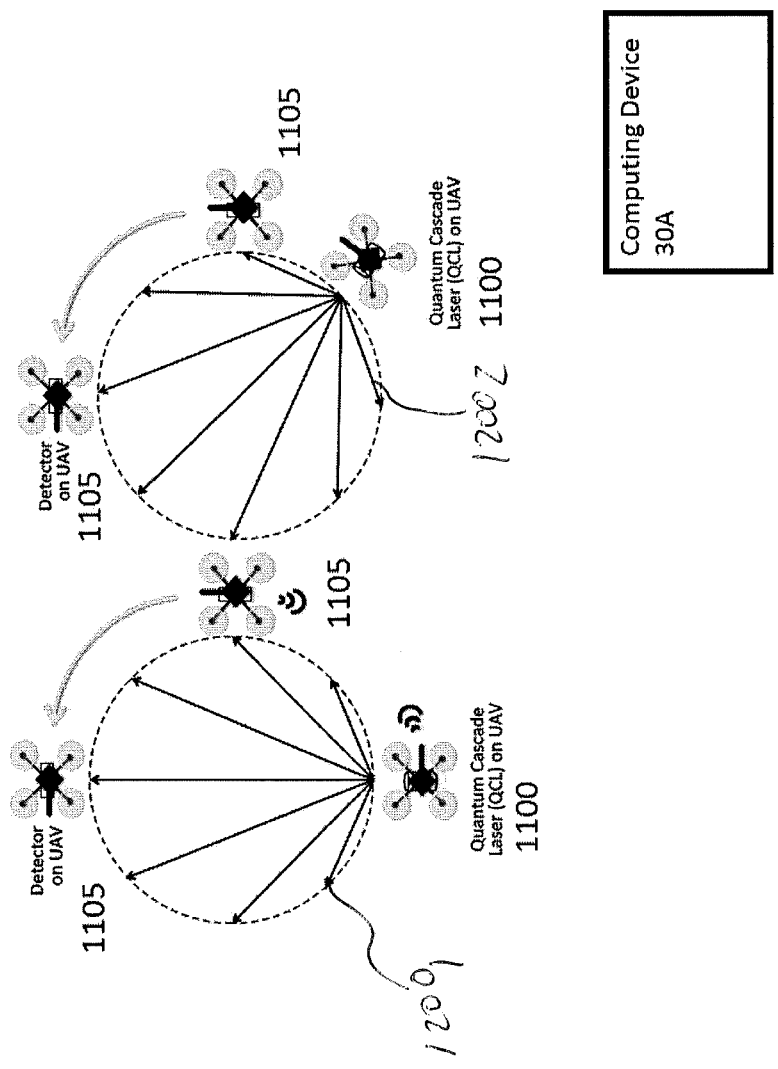

FIG. 11B depicts two sets of LPs from the light source. The first set of LPs $1200_1$ is created when the UAV 1100 is located at one positions and the second set of LPs $1200_2$ is created when the UAV 1100 is at another position. Also as shown in FIG. 11B, the UAV 1105 (with the detector) traverses the perimeter 610A counterclockwise to capture the set of projections (at the various wavelengths), e.g., receive light from each of the light paths). In an aspect of the disclosure UAV 1105 is not required to traverse all 360 degrees of the perimeter 610A. Subsequently, the UAV 1100 relocates to the next position (e.g., right in FIG. 11B) and the UAV 1105 (with detector) traverses the perimeter 610A again to collect the next set of projections.

This process is repeated until the UAV 1100 has completed 180 degree rotation of the perimeter 610A.

Figure 12:
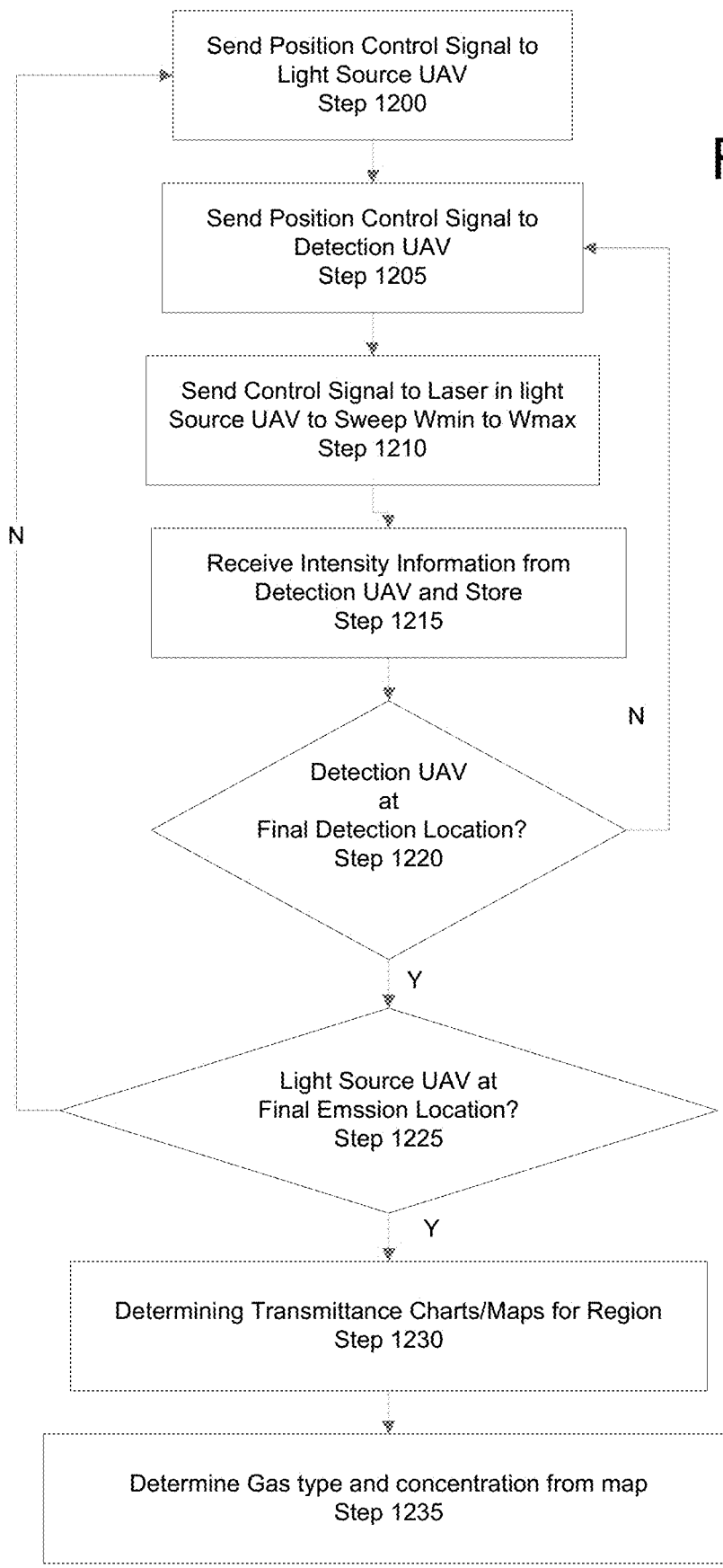
FIG. 12 illustrates a flow chart for controlling UAVs, light source and detection in accordance with aspects of the disclosure.

FIG. 12 illustrates a flow chart for the computing device 30A to determine the presence and distribution of gas emission in accordance with aspects of the disclosure. At steps 1200 and 1205, the computing device 30A transmits position control signals respectively to the UAV having the light source 1100 and the UAV having the detector 1105. Position here refers to both coordinates, e.g., x, y, and z and orientation. In an aspect of the disclosure, prior to deployment of the UAVs, light emission positions and detection positions are predetermined. The detection positions may be equi-distant around the perimeter 610A such as every XX degrees. The number of detection positions increases the resolution of the reconstruction. Similarly, there are multiple emission positions where light can be emitted from the light source. The emission positions may also be equi-distant.

Since the emission and detection positions are predetermined, the orientation of the UAVs in order to have a line of sight for the light source (laser) and detector may also be predetermined. The angle of the light source can be changed based on a change in orientation of the UAV 1100. Similarly, the detection angle may be changed based on a change in orientation of the UAV 1105. The position and orientation of the UAVs 1100/1105 may be confirmation by using of gyroscopes, global position information (GPS), and linear and acceleration sensors, prior to the computing device 30A controlling the light source, e.g., QCL, to emit light.

At step 1210, the computing device 10A sends a control signal to the light source (laser) to sweep the wavelength of the light emitted from Wmin to Wmax at a preset wavelength step. Responsive to the control signal, a control device in the UAV 1100 controls the light source (laser).

The detector in the UAV (1105) detects the intensity of the emitted light, e.g., electrical response in a similar manner as described above. The detector may transmit the electrical response to the computing device 30A or transmit a determined intensity based on the electrical response to the computing device 30A.

At step 1215, the computing device 30A receives the intensity information from the detector (in the UAV).

At step 1220, the computing device 30A determines whether the detection UAV 1105 is located at the final detection location, e.g., completed its rotation. In an aspect of the disclosure, the memory of the computing device 30A includes the position of each detection location and orientation. Further, the memory may include an identifier of the final location or order of the detection locations. The computing device 30A compares the current location of the detection UAV 1105 with the detection locations and order information in memory. If the current location of the detection UAV 1105 is the same location as the final location, then the computing device 30A determines that the UAV 1105 is at the final location ("Y"), otherwise the computing device 30A determines that the detection UAV 1105 is not at the final location. When the UAV 1105 is not at the final location ("N"), the computing device 30A controls the detection UAV 1105 to move to the next position, e.g., return to step 1205. Steps 1205-1220 are repeated for each detection position.

When the detection UAV 1105 is at the final location ("Y"), the computing device 30A determines if the light source UAV 1100 is at the final emission position. In an aspect of the disclosure, the memory of the computing device 30A includes the position of each emission location and orientation. Further, the memory may include an identifier of the final location or order of the emission locations. The computing device 30A compares the current location of the UAV 1100 with the emission locations and order information in memory. If the current location of the light source UAV 1100 is the same location as the final location, then the computing device 30A determines that the UAV 1100 is at the final location ("Y"), otherwise the computing device 30A determines that the emission UAV 1100 is not at the final location.

When the light source UAV 1100 is not at the final location ("N"), the computing device 30A controls the light source UAV 1100 to move to the next emission position, e.g., return to step 1200. Steps 1205-1225 are repeated for each emission position.

When the light source UAV 110 is at the final emission position ("Y"), the computing device 30A uses the reconstruction techniques described above to generate reconstructed images for the area of interest. The reconstructed images are aggregated to generate attenuation spectrum (or transmittance charts) for each voxel within the area of interest. Using the generated attenuation spectrum (or transmittance charts) for each voxel, the computing device 30A determines the gas type and distribution at step 1235. Concentration of a gas at a specific voxel may also be determined by the peak value.

Testing

Figure 13:
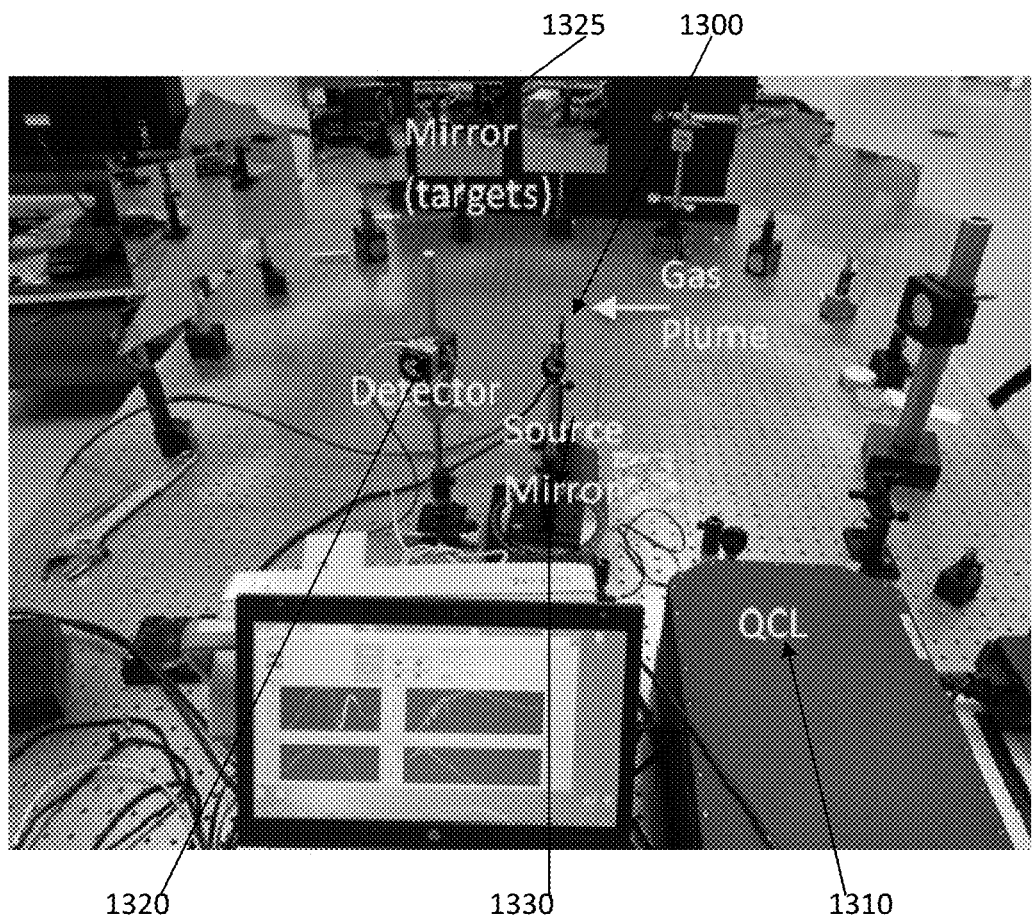
FIG. 13 is a photograph depicting a test setup for a system in accordance with aspects of the disclosure.

Aspects of the disclosure were tested using the test setup shown in the photograph of FIG. 13. The test setup places an array of 11 mirrors (collectively 1325) around a 48" diameter circle. The light source was a QCL 1310. For this smaller scale setup, a few modifications in the system geometry were made for ease of setup. To ease the rotational motion requirements for the source, a mirror 1330 was used for the source spot and the detector 1320 is offset from the source location. In this configuration, only the mirror is required to be placed on a rotational stage. The QCL 1310 was aimed at the source mirror 1330 causing an additional path through the area that is included in every projected ray.

To ease control requirements on additional mirrors for reprojection of the source, an object containing the gas, e.g., plume was moved in a circular rotation within the system to provide rotated projections.

Figure 14:
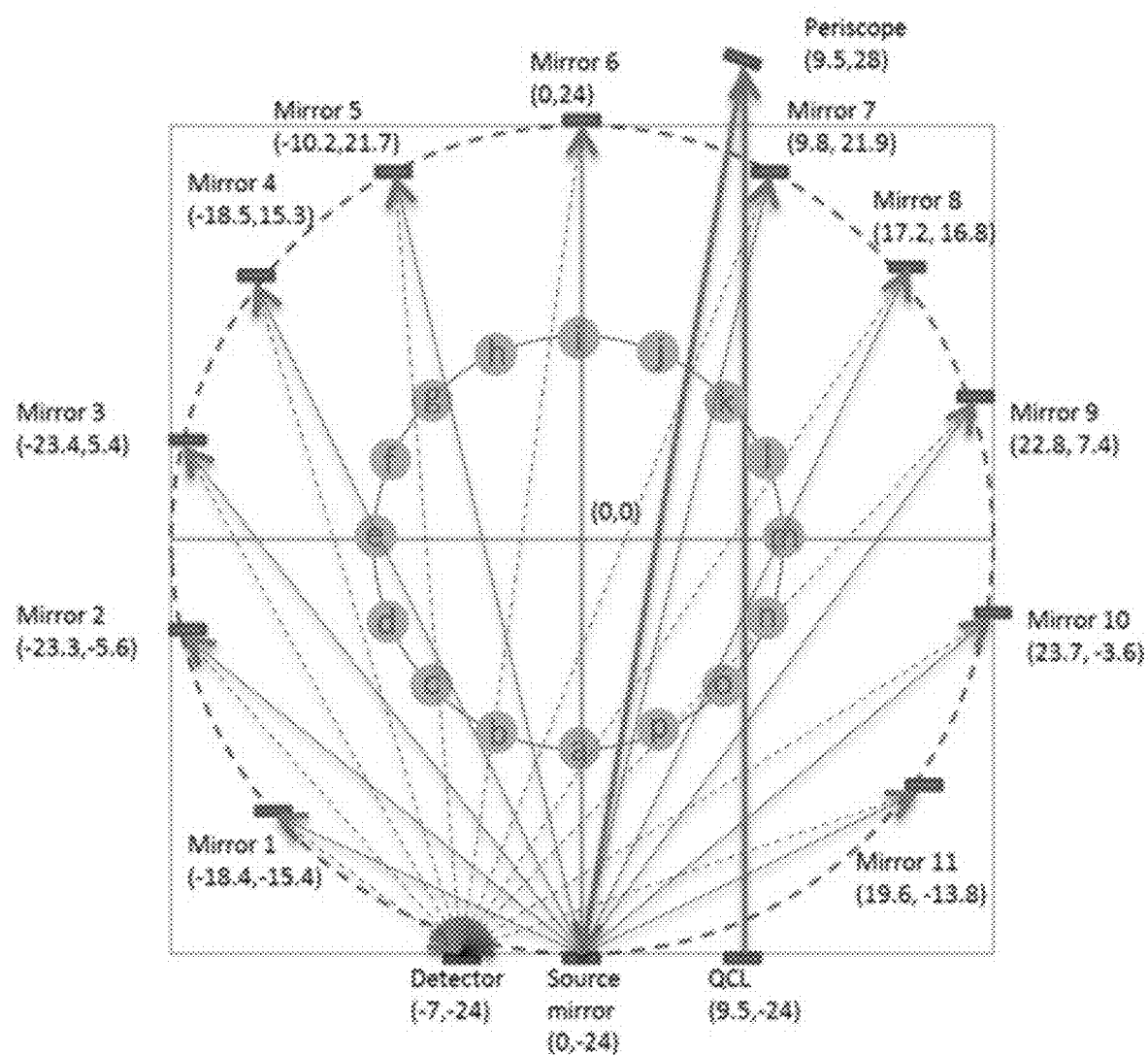
FIG. 14 illustrates the test setup layout and light paths.

As seen in FIG. 14, the QCL 1310 was placed next to the source mirror 1330 requiring two light rays to pass through the detection area. Light rays (showing as both solid lines and dashes) show all the paths associated with measurement of a single projection. The light ray between the QCL 1310 (identified as solid line) and the periscope 1400 is close to the table below the measurement plane by approximately 6" and the periscope 1400 returns a ray in the measurement plane to the source mirror. Rotation of the source mirror 1330 selects a mirror (one of the mirrors 1325) for measurement and each of those mirrors were set to return the light to the detector 1320 at the location. Separation of the source location and the detector resulted in a more complex ray path as the transmitted and reflected rays do not pass through the same path.

For the test object, a gas cylinder containing a concentration of 5% methane was used. The tube was placed just below the measurement plane to provide a plume of gas 1300 in the plane. Instead of rotating the measurement system around the plume, projections were captured by moving the plume in a circular pattern represented by the dots on the inner circle which is 24" in diameter.

16 projections were captured in this manner with 11 mirrors providing different rays (11 pixels) per projection. A four module QCL system is able to scan the laser, collect, display and record data in about 45 seconds per scan for a single mirror.

Figure 15:
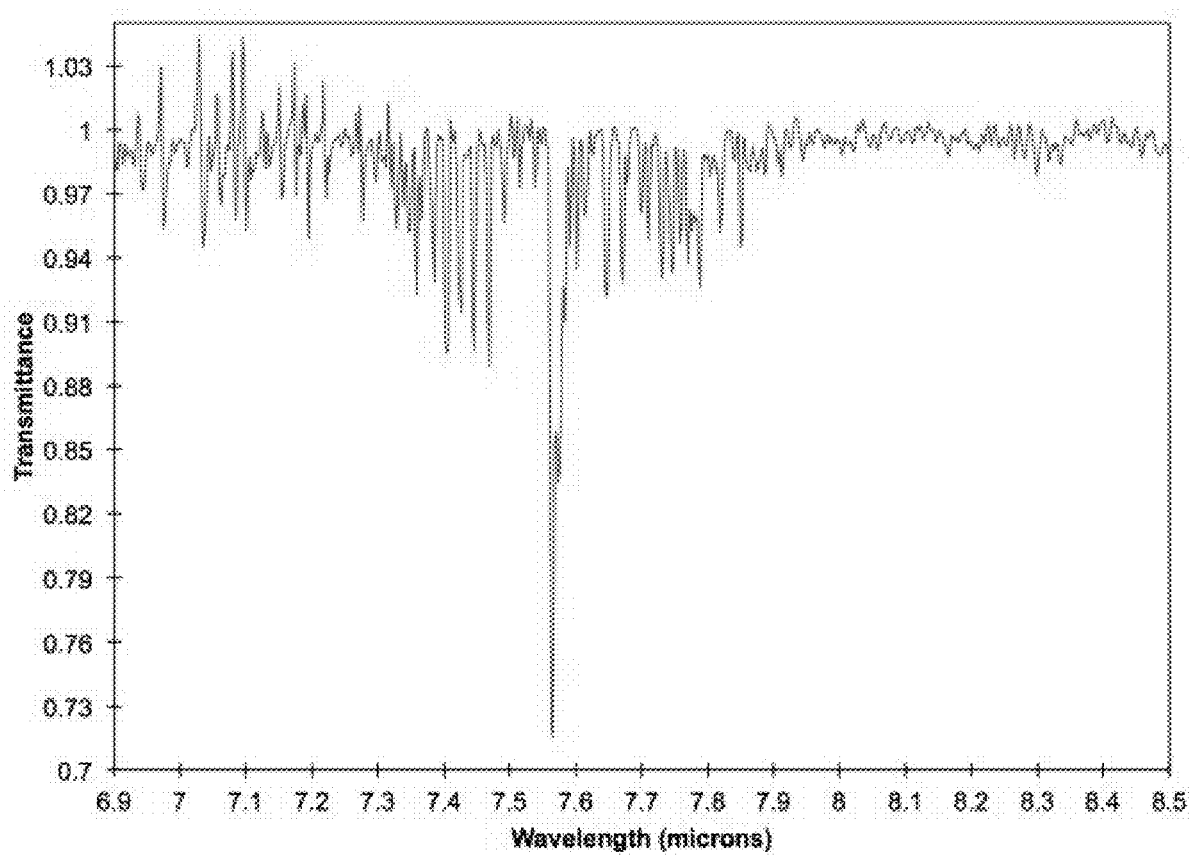
FIG. 15 illustrates an example of a transmittance plot.

The QCL 1310 included one QCL module with a wavelength range from 6.87-8.52 um (which corresponds to $CH_4$ absorption region). Each location measurement ray through the system was captured at 808 equally spaced wavelengths (2 nm steps) within the range. Multiple transmittance plots were obtained. For example, FIG. 15 illustrates an example of a transmittance plot using data from a measurement using mirror 6 with the gas plume located in position "a", the closest position to the source mirror, and thus indicates the attenuation along one ray. The large attenuation between 7.5 and 7.6 μm is Methane's absorption peak.

Using the spectral data for each projection pixel, a reconstruction was performed for each wavelength bin using the CT reconstruction techniques described above and a modified system matrix including the offset between the source and detector locations.

Figure 16A:
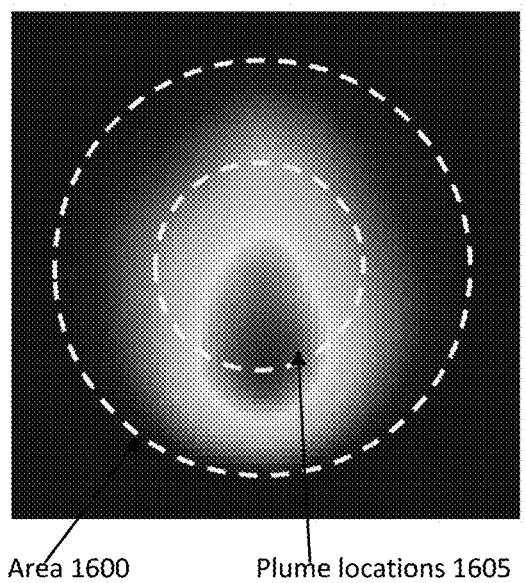
FIGS. 16A and 16B are examples of reconstructed images at the 7.656 μm wavelength bin where

FIG. 16A is an example of one of the reconstructed image at the 7.656 um wavelength bin placing a peak near the source location as expected for the data set.

Figure 16B:
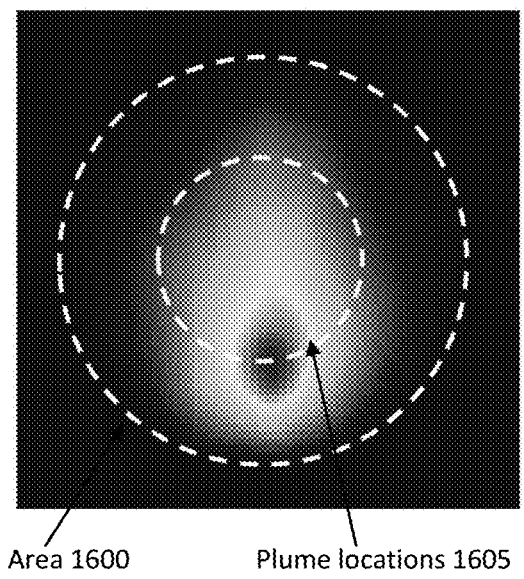

FIG. 16A is reconstructed with both interpolation in a projection space and smoothing filters in a voxel space. FIG. 16B also shows an example of a reconstructed image at the 7.656 um wavelength bin (same wavelength bin) placing a peak near the source location as expected for the data set; however, for the reconstructed image in FIG. 16B smoothing filters in the voxel space were used without interpolation in the projection space. A 3×3 mean filter was used for both. 10 rays (pixels) were interpolated between each detected ray (pixel) to reconstruct the image in FIG. 16A. There were 111 pixels in each projection (100 interpolated and 11 detected) used to generate the reconstructed image depicted in FIG. 16A. As can be seen from FIGS. 16A and 16B, the use of interpolation in conjunction with mean filters causes a spatial expansion of the plume area.

Figure 17:
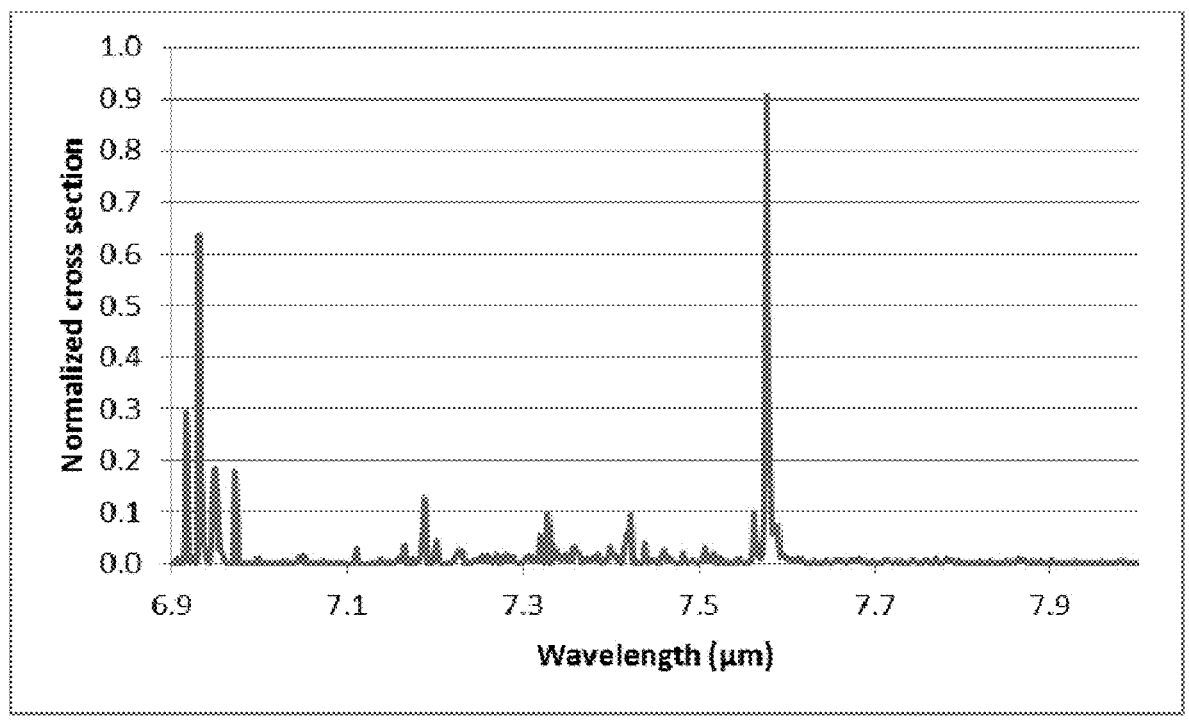
FIGS. 17 and 18 respectively illustrate a plot of the spectrum for a respective voxel, where in FIG. 17 the voxel is located on the plume location and in FIG. 18 the voxel is away from the plume.
Figure 18:
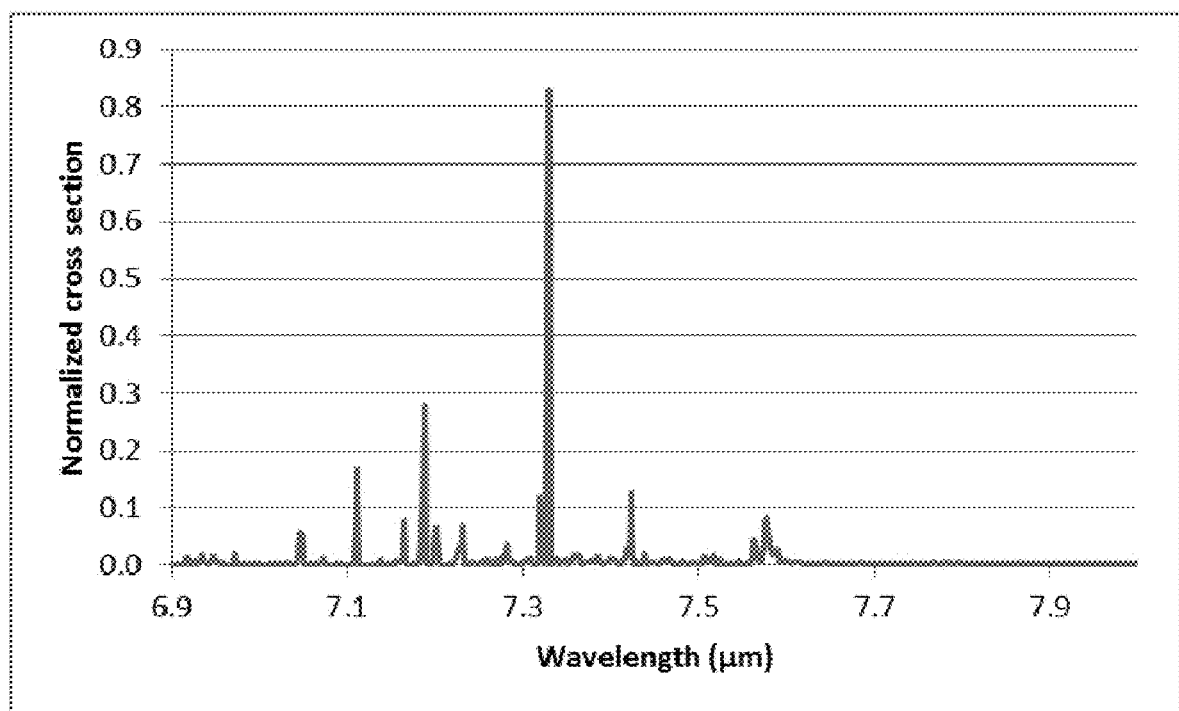

Each voxel in the reconstructed plan has an associated spectrum. FIG. 17 contains a plot of the spectrum for a voxel located on the plume location and FIG. 18 for a voxel away from the plume. FIGS. 17 and 18 were based on a series of reconstructed images generated in the same manner as the reconstructed image in FIG. 16B. As can be seen from FIGS. 17 and 18, the peak (in this case methane peak) is strong at the 7.65 μm wavelength when on the plume location than when away from the plume location. The peak may be correlated to a concentration at a given voxel.

Various aspects of the present disclosure may be embodied as a program, software, or computer instructions embodied or stored in a computer or machine usable or readable medium, or a group of media which causes the computer or machine to perform the steps of the method when executed on the computer, processor, and/or machine. A program storage device readable by a machine, e.g., a computer readable medium, tangibly embodying a program of instructions executable by the machine to perform various functionalities and methods described in the present disclosure is also provided, e.g., a computer program product.

The computer readable medium could be a computer readable storage device or a computer readable signal medium. A computer readable storage device, may be, for example, a magnetic, optical, electronic, electromagnetic, infrared, or semiconductor system, apparatus, or device, or any suitable combination of the foregoing; however, the computer readable storage device is not limited to these examples except a computer readable storage device excludes computer readable signal medium. Additional examples of the computer readable storage device can include: a portable computer diskette, a hard disk, a magnetic storage device, a portable compact disc read-only memory (CD-ROM), a random access memory (RAM), a read-only memory (ROM), an erasable programmable read-only memory (EPROM or Flash memory), an optical storage device, or any appropriate combination of the foregoing; however, the computer readable storage device is also not limited to these examples. Any tangible medium that can contain, or store, a program for use by or in connection with an instruction execution system, apparatus, or device could be a computer readable storage device.

A computer readable signal medium may include a propagated data signal with computer readable program code embodied therein, such as, but not limited to, in baseband or as part of a carrier wave. A propagated signal may take any of a plurality of forms, including, but not limited to, electromagnetic, optical, or any suitable combination thereof. A computer readable signal medium may be any computer readable medium (exclusive of computer readable storage device) that can communicate, propagate, or transport a program for use by or in connection with a system, apparatus, or device. Program code embodied on a computer readable signal medium may be transmitted using any appropriate medium, including but not limited to wireless, wired, optical fiber cable, RF, etc., or any suitable combination of the foregoing.

The terms "Processor", "Computing Device" and "Controller" as may be used in the present disclosure may include a variety of combinations of fixed and/or portable computer hardware, software, peripherals, and storage devices. The "Processor", "Computing Device" "Controller" may include a plurality of individual components that are networked or otherwise linked to perform collaboratively, or may include one or more stand-alone components. The hardware and software components of the "Processor", "Computing Device" and/or "Controller" of the present disclosure may include and may be included within fixed and portable devices such as desktop, laptop, and/or server, and network of servers (cloud).

The terminology used herein is for the purpose of describing particular embodiments only and is not intended to be limiting the scope of the disclosure and is not intended to be exhaustive. Many modifications and variations will be apparent to those of ordinary skill in the art without departing from the scope and spirit of the disclosure.

What is claimed is:

1. A system for determining a presence and distribution of gas emissions in an area comprising:
    a plurality of light detectors disposed around a perimeter of an area;
    a light source configured to emit light at a plurality of wavelengths towards each of the plurality of light detectors, whereby for each of the plurality of light detectors, the light is received at each of the plurality of wavelengths; and
    one or more processors configured to receive information representing light intensity detected by each of the plurality of light detectors, respectively at each of the plurality of wavelengths and determine gases present in each of a plurality of voxels within the area, where a voxel represents a location within the area on reconstructed images of the area, based on the receive information representing light intensity detected by the respective detector at each of the plurality of wavelengths and a distribution thereof, wherein the light intensity detected by the respective detector includes reflected light received via at least one reflector, wherein the at least one reflector is configured to rotate such that the emitted light at each of the plurality of wavelengths is reflected towards different detectors once a detector has received the emitted light at each of the plurality of wavelengths, and wherein the determination of the gas present at each of the plurality of voxels is further based on angle information indicating an angle of each of the at least one reflector.

2. The system for determining the presence and distribution of gas emissions according to claim 1, wherein the light source is configured to rotate to emit light to each of the plurality of light detectors.

3. The system for determining the presence and distribution of gas emissions according to claim 1, wherein one of the at least one reflector is disposed in front of the light source, the one of the at least one reflector being configured to rotate to emit light to each of the plurality of light detectors after the plurality of wavelengths have been emitted to a respective detector.

4. The system for determining the presence and distribution of gas emissions according to claim 1, wherein the light source is a quantum cascade laser system configured to emit infrared light.

5. The system for determining the presence and distribution of gas emissions according to claim 4, wherein the quantum cascade laser system is configured to emit light between 3 µm to 16 µm.

6. The system for determining the presence and distribution of gas emissions according to claim 1, wherein each of the plurality of light detectors is located in a respective predetermined position and the light is emitted at a preset angle towards each of the plurality of light detectors.

7. The system for determining the presence and distribution of gas emissions according to claim 6, wherein the at least one reflector comprising a plurality of reflectors, each reflector corresponding to a respective detector, each reflector being configured to rotate such that the emitted light at each of the plurality of wavelengths is reflected towards different detectors once a detector has received the emitted light at each of the plurality of wavelengths.

8. The system for determining the presence and distribution of gas emissions according to claim 7, wherein the one or more processors is configured to receive information representing light intensity detected by each of the plurality of light detectors respectively at each of the plurality of wavelengths directly from the light source and information representing an intensity of reflected light respectively detected at each of the plurality of detectors at each of the plurality of wavelengths, being reflected by one or more of the plurality of reflectors, and determine gases present in each voxel, based on the received information.

9. The system for determining the presence and distribution of gas emissions according to claim 8, wherein the one or more processors determines the gases for each voxel within the area by determining attenuation, at each of the plurality of wavelengths, from information representing light detected by each of the plurality of light detectors respectively at each of the plurality of wavelengths directly from the light source and information representing the intensity of reflected light respectively detected at each of the plurality of detectors at each of the plurality of wavelengths, being reflected by one or more of the plurality of reflectors.

10. The system for determining the presence and distribution of gas emissions according to claim 9, wherein the attenuation, at each of the plurality of wavelengths, is determined using a tomographic reconstruction technique and interpolating intensity information for additional light paths between light paths created by the source and the plurality of reflectors to the plurality of detectors.

11. The system for determining the presence and distribution of gas emissions according to claim 7, wherein the one or more processors is also configured to receive angle information representing an angle of the reflector, the angle information being used to determine a respective light path.

12. The system for determining the presence and distribution of gas emissions according to claim 7, further comprising a retroreflector and one of the plurality of detectors is co-located with the light source.

13. The system for determining the presence and distribution of gas emissions according to claim 6, further comprising a reflector co-located with each of the plurality of detectors, each reflector configured to rotate at a second preset angle such that the emitted light at each of the plurality of wavelengths is reflected towards each of the other plurality of detectors, wherein the light source is configured to repeatedly emit light at each of the plurality of wavelengths for a respectively detector for each of the second preset angles.

14. The system for determining the presence and distribution of gas emissions according to claim 1, wherein the plurality of light detectors are moveable around the perimeter of the area.

15. The system for determining the presence and distribution of gas emissions according to claim 14, wherein the plurality of light detectors are located on unmanned aerial vehicles and wherein the unmanned aerial vehicle move around a perimeter of the area.

16. The system for determining the presence and distribution of gas emissions according to claim 15, wherein the light source is located on an unmanned aerial vehicle and the unmanned aerial vehicle moves at least partially around the perimeter of the area.

17. The system for determining the presence and distribution of gas emissions according to claim 16, wherein the one or more processors is configured to determine the gases for each voxel within the area by determining attenuation at each voxel, at each of the plurality of wavelengths, from information representing light intensity detected by the plurality of detectors respectively.

18. The system for determining the presence and distribution of gas emissions according to claim 16, wherein the one or more processors is configured to control the position of the unmanned aerial vehicles having the light source and the plurality of light detectors, respectively.

19. The system for determining the presence and distribution of gas emissions according to claim 1, wherein each detector further includes a transmitter configured to transmit information representing light intensity detected to the one or more processors.

20. A system for determining a presence and distribution of gas emissions comprising:
    a plurality of reflectors, or a plurality of retroreflectors disposed around a perimeter of an area;
    a light detector disposed on the perimeter of the area;
    a light source configured to emit light at a plurality of wavelengths towards each of the plurality of reflectors or retroreflectors, whereby for each of the plurality of reflectors or retroreflectors, the light is reflected at each of the plurality of wavelengths to a single light detector via light paths; and
    a processor configured to receive information representing light intensity detected by the detector, respectively at each of the plurality of wavelengths and determine gases present in each of a plurality of voxels within the area, where a voxel represents a location within the area on reconstructed images of the area based on the receive information representing the light intensity detected by the detector at each of the plurality of wavelengths and a distribution thereof, wherein at least one of the light source or one or more of the plurality of reflectors or retroreflectors are configured to rotate to change a light path and and wherein the determination of the gas present at each of the plurality of voxels is further based on angle information indicating an angle of the light source and the plurality of reflectors or retroreflectors.

* * * * *